(12) United States Patent
Sennlaub et al.

(10) Patent No.: US 11,072,661 B2
(45) Date of Patent: Jul. 27, 2021

(54) AGENTS THAT INHIBIT THE BINDING OF CFH TO CD11 B/CD18 AND USES THEREOF

(71) Applicants: SORBONNE UNIVERSITE, Paris (FR); CENTRE NATIONAL DE LA RECHERCHE SCIENTIFIQUE, Paris (FR); INSERM (Institut National de la Santé et de la Recherche Médicale), Paris (FR)

(72) Inventors: Florian Sennlaub, Paris (FR); Bertrand Callippe, Paris (FR); Xavier Guillonneau, Boulogne Billancourt (FR); José-Alain Sahel, Paris (FR)

(73) Assignees: SORBONNE UNIVERSITE, Paris (FR); CENTRE NATIONAL DE LA RECHERCHE SCIENTIFIQUE (CNRS), Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 0 days.

(21) Appl. No.: 16/066,015

(22) PCT Filed: Dec. 23, 2016

(86) PCT No.: PCT/EP2016/082540
§ 371 (c)(1),
(2) Date: Jun. 25, 2018

(87) PCT Pub. No.: WO2017/109164
PCT Pub. Date: Jun. 29, 2017

(65) Prior Publication Data
US 2019/0010235 A1 Jan. 10, 2019

(30) Foreign Application Priority Data
Dec. 23, 2015 (EP) .................................... 15202603

(51) Int. Cl.
A61K 39/00 (2006.01)
C07K 16/28 (2006.01)
A61P 27/02 (2006.01)
A61P 29/00 (2006.01)
A61K 9/00 (2006.01)

(52) U.S. Cl.
CPC ........ *C07K 16/2845* (2013.01); *A61K 9/0014* (2013.01); *A61K 9/0048* (2013.01); *A61P 27/02* (2018.01); *A61P 29/00* (2018.01); *A61K 2039/505* (2013.01); *A61K 2039/54* (2013.01); *C07K 2317/76* (2013.01)

(58) Field of Classification Search
None
See application file for complete search history.

(56) References Cited

U.S. PATENT DOCUMENTS

| 5,567,440 A * | 10/1996 | Hubbell | A61K 9/5031 424/484 |
| 6,524,581 B1 * | 2/2003 | Adamis | A61K 9/0048 424/130.1 |
| 2004/0028648 A1 * | 2/2004 | Adamis | A61K 31/7088 424/85.1 |
| 2008/0220003 A1 * | 9/2008 | Schnatbaum | C07C 235/40 424/178.1 |
| 2009/0036405 A1 * | 2/2009 | Kennedy | A61K 31/727 514/56 |
| 2016/0139120 A1 * | 5/2016 | Barile | C07K 16/28 424/139.1 |

FOREIGN PATENT DOCUMENTS

| EP | 2898896 | 7/2015 |
| WO | 89-04174 | 5/1989 |
| WO | 93/06865 A1 | 4/1993 |
| WO | 2004-032861 | 4/2004 |
| WO | 2006-088950 | 8/2006 |
| WO | 2007-056227 | 5/2007 |
| WO | 2008-008986 | 1/2008 |
| WO | 2011-137363 | 11/2011 |
| WO | 2014-060517 | 4/2014 |
| WO | 2015-120130 | 8/2015 |

OTHER PUBLICATIONS

Whitcup et al. Monoclonal Antibody Against CDIIb/CD 18 Inhibits Endotoxin-Induced Uveitis. Invest Ophthalmol Vis Sci. 1993;34:673-681. (Year: 1993).*
Rosen, H. et al. (1989) Antibody to the murine type 3 complement receptor inhibits T lymphocyte-dependent recruitment of myelomonocytic cells in vivo. J Exp Med. 169: 535-48. (Year: 1989).*
Kim, Soo-Young. Retinal phagocytes in age-related macular degeneration. Macrophage (Houst). Jun. 5, 2015 ; 2(1) (Year: 2015).*
Apte et al. Macrophages Inhibit Neovascularization in a Murine Model of Age-Related Macular Degeneration. PLoS Med. Aug. 2006; 3(8):e310. (Year: 2006).*
Ambati et al. An animal model of age-related macular degeneration in senescent Ccl-2- or Ccr-2-deficient mice. Nat Med . Nov. 2003;9(11):1390-7). (Year: 2003).*
Combadiere et al., "CX3CR1-dependent subretinal microglia cell accumulation is associated with cardinal features of age-related macular degeneration". Journal of Clinical Investigation. 2007, 117:2920-2928.
Cruz-Guilloty et al., "Infiltration of proinflammatory m1 macrophages into the outer retina precedes damage in a mouse model of age-related macular degeneration". International Journal of Inflammation. 2013, 2013:503725.

(Continued)

*Primary Examiner* — Maher M Haddad
(74) *Attorney, Agent, or Firm* — Nixon & Vanderhye

(57) ABSTRACT

Disclosed are agents inhibiting the interaction between CFH and CD11b/18, as well as the use of such agents, in particular for treating inflammatory disorders, such as age-related macular degeneration.

6 Claims, 8 Drawing Sheets

(56) References Cited

OTHER PUBLICATIONS

Despriet et al., "Complement Factor H Polymorphism, Complement Activators, and Risk of Age-Related Macular Degeneration". Journal of the American Medical Association. 2006, 296:301-309.
Dewan et al., "HTRA1 promoter polymorphism in wet age-related macular degeneration". Science. 2006, 314 (5801):989-992.
Discipio et al., "Human polymorphonuclear leukocytes adhere to complement factor H through an interaction that involves alphaMbeta2 (CD11b/CD18)". Journal of Immunology, 1998, 160:4057-4066.
Edwards et al., "Complement factor H polymorphism and age-related macular degeneration". Science. 2005, 308 (5720):421-424.
Fritsche et al., "Seven new loci associated with age-related macular degeneration". Nature Geneteics. 2013, 45:433-439.
Gautier et al., "Gene-expression profiles and transcriptional regulatory pathways that underlie the identity and diversity of mouse tissue macrophages". Nature Immunology. 2012, 13:1118-1128.
Glass et al., "Mechanisms Underlying Inflammation in Neurodegeneration". Cell. 2010, 140:918-934.
Grivennikov et al., "Immunity, Inflammation, and Cancer". Cell. 2010, 140:883-899.
Gupta et al., "Activated microglia in human retinitis pigmentosa, late-onset retinal degeneration, and age-related macular degeneration". Experimental Eye Research. 2003, 76(4):463-471.
Haines et al., "Complement factor H variant increases the risk of age-related macular degeneration". Science. 2005, 308(5720):419-421.
Hakobyan et al., "Variant-specific quantification of factor H in plasma reveals null alleles associated with atypical hemolytic uremic syndrome". Kidney International. 2010, 78(8):782-8.
Hotamisligil, "Endoplasmic Reticulum Stress and the Inflammatory Basis of Metabolic Disease". Cell. 2010, 140:900-917.
Kang Yu-Hoi et al., "Human complement Factor H modulates C1q-mediated phagocytosis of apoptotic cells". Immunobiology, 2011, 217 :455-464.
Klein et al., "The epidemiology of age-related macular degeneration". American Journal of Ophthalmology 2004, 137(3):486-495.
Lavalette et al., "Interleukin-1β inhibition prevents choroidal neovascularization and does not exacerbate photoreceptor degeneration". American Journal of Pathology May 2011;178(5):2416-23.
Levy et al., "Apolipoprotein E promotes subretinal mononuclear phagocyte survival and chronic inflammation in age-related macular degeneration". EMBO Molecular Medicine 2015, 7(2):211-226.
Losse et al., "Factor H and factor H-related protein 1 bind to human neutrophils via complement receptor 3, mediate attachment to Candida albicans, and enhance neutrophil antimicrobial activity". Journal of Immunology, 2010, 184:912-921.
Pickering et al., "Uncontrolled C3 activation causes membranoproliferative glomerulonephritis in mice deficient in complement factor H". Natutre Genetics 2002, 31:424-428.
Rayes et al., "Mutation and ADAMTS13-dependent modulation of disease severity in a mouse model for von Willebrand disease type 2B". Blood. 2010, 115:4870-4877.
Rosen & Gordon, "Monoclonal antibody to the murine type 3 complement receptor inhibits adhesion of myelomonocytic cells in vitro and inflammatory cell recruitment in vivo". Journal of Experimental Medicine. 1987, 166, 1685-1701.
Schlaf et al., "Expression and regulation of complement factors H and I in rat and human cells: some critical notes". Molecular immunology. 2001, 38:231-239.
Seddon et al., "Dietary carotenoids, vitamins A, C, and E, and advanced age-related macular degeneration. Eye Disease Case-Control Study Group". Eye Disease Case-Control Study Group Journal of the American Medical Association. 1994, 272(18):1413-1420.
Sennlaub et al., "CCR2(+) monocytes infiltrate atrophic lesions in age-related macular disease and mediate photoreceptor degeneration in experimental subretinal inflammation in Cx3cr1 deficient mice". EMBO Molecular Medicine 2013, 5(11):1775-1793.
Thompson et al., "Complement factor H and hemicentin-1 in age-related macular degeneration and renal phenotypes". Human Molecular Genetics 2007, 16:2135-2148.
Tsutsumi et al., "The critical role of ocular-infiltrating macrophages in the development of choroidal neovascularization". Journal of Leukocyte Biology 2003, 74(1):25-32.
Weismann et al., "Complement factor H binds malondialdehyde epitopes and protects from oxidative stress". Nature. 2011, 478:76-81.
Yang et al., "A variant of the HTRA1 gene increases susceptibility to age-related macular degeneration". Science. 2006,314(5801):992-993.
Zipfel et al., "Factor H family proteins: on complement, microbes and human diseases". Biochemical Society Transactions 2002, 30:971-978.
International Search Report of PCT application WO2017109164 (dated Mar. 14, 2017).
Huituinga et al., "Treatment with anti-CR3 antibodies ED7 and ED8 suppresses experimental allergic encephalomyelitis in Lewis rats", European Journal of Immunology, vol. 23, No. 3, Mar. 1993, pp. 709-715.
Palmen et al., "Anti-CD11b/CD18 antibodies reduce inflammation in acute colitis in rats", Clinical and Experimental Immunology, vol. 101, No. 2, Aug. 1995, pp. 351-356.
Yoshida et al., "Activated monocytes induce human retinal pigment epithelial cell apoptosis through caspase-3 activation", Laboratory Investigation, vol. 83, No. 8, Aug. 2003, pp. 1117-1129.
Staunton et al., "Targeting integrin structure and function in disease", Advcances in Immunology, vol. 91, 2006, pp. 111-157.

* cited by examiner

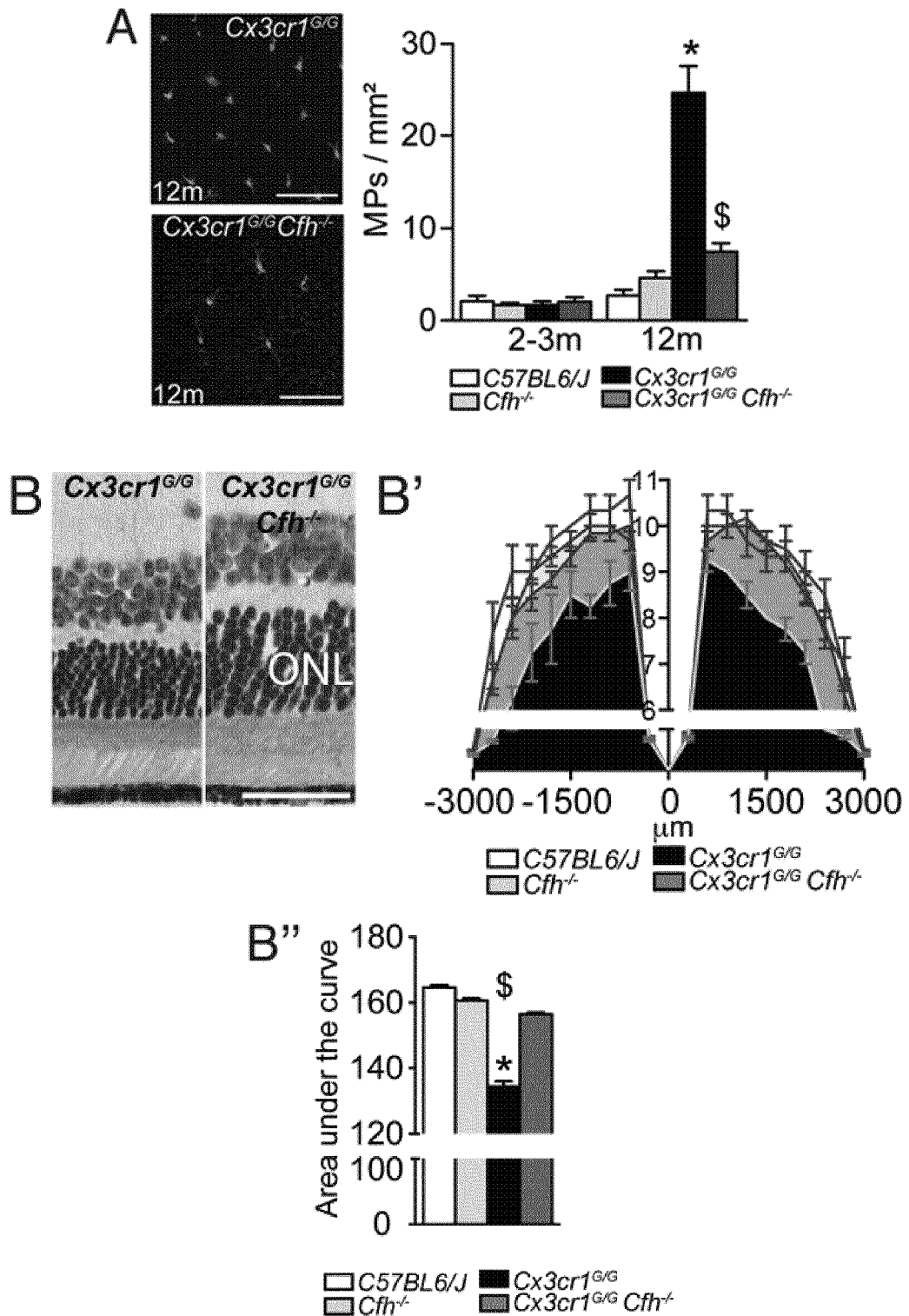
FIG. 1A-B"

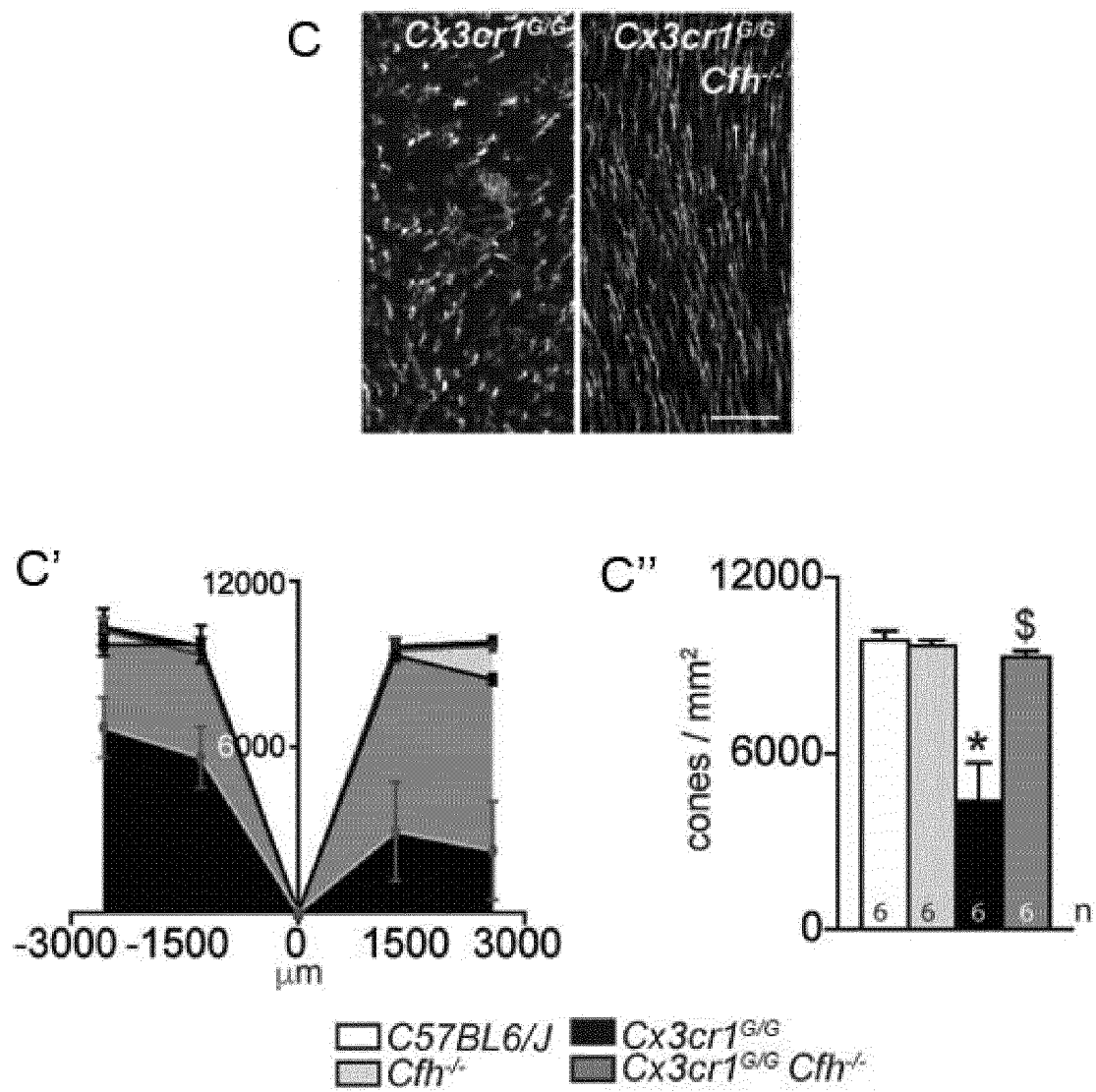
FIG. 1C-C"

AGENTS THAT INHIBIT THE BINDING OF CFH TO CD11 B/CD18 AND USES THEREOF

FIELD OF INVENTION

The present invention relates to agents that inhibit the interaction of Complement Factor H with CD11b/CD18. The present invention also relates to the treatment of inflammatory disorders and diseases, such as age related macular degeneration.

BACKGROUND OF INVENTION

Age related macular degeneration (AMD) is the leading cause of legal blindness in the developed world. There are two clinical forms of late AMD: the fast developing exudative form ("wet" AMD) defined by choroidal neovascularisation (CNV) and the more slow developing atrophic form characterized by retinal pigment epithelium (RPE) atrophy and the photoreceptor degeneration known as geographic atrophy (GA, or late stage "dry" AMD). Although AMD is often classified into "atrophic" and "wet" forms, they both develop on an inflammatory background and are associated with the same polymorphisms such as those of Complement Factor-H (CFH) (Haines et al., Science. 2005, 308:419-421; Edwards et al., Science. 2005, 308:421-424), Serine Protease High Temperature Requirement A1 (HTAR1) and Age-Related Maculopathy Susceptibility 2 (ARMSD2) (Dewan et al., Science. 2006, 314:989-992; Yang et al., Science. 2006, 314:992-993).

Mononuclear phagocytes (MP) comprise a family of cells that include microglial cells (MC), monocytes (Mo), and macrophages (Mφ). Physiologically, MCs are present only in the inner retina. The subretinal space, located between the retinal pigment epithelium (RPE) and the photoreceptor outer segments (POS), is a zone of immune privilege mediated by immunosuppressive RPE signals, including leukocyte suppressing FasL (CD95L). Nevertheless, MPs accumulate in the subretinal space in the two advanced forms of sight-threatening AMD (Klein et al., Am J Ophthalmol. 2004, 137:486-495). They are in close contact with the RPE in choroidal neovascularisation and in the vicinity of the RPE lesion in geographic atrophy (Gupta et al., Exp Eye Res. 2003, 76:463-471; Sennlaub et al., EMBO Mol Med. 2013, 5:1775-1793). MPs are thought to contribute to CNV (Tsutsumi et al., J Leukoc Biol. 2003, 74:25-32) and to photoreceptor degeneration in GA (Cruz-Guilloty et al., Int J Inflam. 2013, 2013:503725). It was recently showed that subretinal MPs are also present in and around soft drusen, that are an important risk factor to develop late AMD (Sennlaub et al., EMBO Mol Med. 2013, 5:1775-1793; Levy et al., EMBO Mol Med. 2015, 7:211-226). Nevertheless, the reasons for the alteration of subretinal immunosuppression and subsequent accumulation of MPs in AMD remain unknown.

No medical or surgical treatment is available for the "dry" condition, however vitamin supplements with high doses of antioxidants, lutein and zeaxanthin, have been suggested to slow the progression (Seddon et al., Eye Disease Case-Control Study Group JAMA. 1994, 272:1413-1420).

There are known treatments for wet AMD, such as the use of anti-neovascular agents and photodynamic therapy (laser irradiation of the macula). Anti-neovascular agents for treatment of wet AMD include agents which block the action of vascular endothelial growth factor (VEGF) thereby slowing angiogenesis (formation of new blood vessels in the retina) which leads to choroidal neovascularization and loss of vision in wet AMD patients. Such "anti-VEGF" agents approved or in clinical study for treating wet AMD include bevacizumab (AVASTIN™), ranibizumab (LUCENTIS™), and aflibercept (EYLEA™).

New proposals of treatments are described, for example, in WO2008008986, which disclose the administration of CFHR1 and/or CFHR3 polypeptide. The international patent application WO2011137363 is directed to the reduction of 5-lipoxygenase (5-LO) activity to treat age-related macular degeneration. Another example is WO2014060517 which concerns the administration of a RdCVFL polynucleotide or polypeptide to a subject to treat AMD.

However, no drug is currently on the market for treating dry AMD or geographic atrophy. AMD is associated with non-resolving and low-grade chronic inflammation (Combadiere et al., J Clin Invest. 2007, 117:2920-2928; Levy et al., EMBO Mol Med. 2015, 7:211-226). More generally, inflammation is the organism's response to tissue injury and microbial invasion. Ideally, it quickly and efficiently eliminates pathogens and repairs the tissue injury either by regeneration or scarring. If the inflammatory response is not quickly controlled, it can become pathogenic and contribute to disease progression, as seen in many chronic inflammatory diseases. Nonresolving and low-grade chronic inflammation is observed in contexts such as metabolic diseases (obesity, atherosclerosis) (Hotamisligil, Cell. 2010, 140:900-917), neurodegenerative diseases (Glass et al., Cell. 2010, 140:918-934) and cancers (Grivennikov et al., Cell. 2010, 140:883-899). Nonresolving inflammation is not a primary cause of these diseases, but it contributes significantly to their pathogenesis as microbicidal mediators produced by neutrophils and interstitial macrophages (reactive oxygen species, proteases and inflammatory cytokines . . . ) can also cause considerable collateral damages to host cells, which itself causes more inflammation. It is often not clear to what extent chronic inflammation persists because of a continuous primary problem or to the incapacity to exit the cycle of inflammation, collateral damage, and renewed inflammation.

In view of these elements, there is therefore still an ongoing need for identifying active ingredients for preventing and/or treating inflammation, more specifically inflammation associated with mononuclear phagocytes accumulation, and more particularly AMD.

The Applicant surprisingly demonstrated that Complement Factor H (CFH) inhibits MP elimination and participates to the MP accumulation. In particular, the Applicant shows that CFH plays this inhibitory role through its interaction with the integrin CD11b/CD18.

Complement Factor H is known to be associated with the risk of geographic atrophy (Fritsche et al., Nat Genet. 2013, 45:433-439) and the presence of a CFH risk allele may be used to diagnose GA, as described for example in WO2006088950 and WO2015120130. However, the role of Complement Factor H to inhibit MP elimination in the mechanism of inflammation mediated by MPs accumulation was for the first time shown by the Applicant.

Therefore, the present invention relates to agents that inhibit Complement Factor H interaction with CD11b/CD18 and their use in the treatment of inflammatory disorders, such as age related macular degeneration.

SUMMARY

The present invention relates to an agent inhibiting the binding of Complement Factor H to CD11b/CD18 for use for treating inflammation.

In one embodiment, said agent binds to CD11b/CD18.

In a particular embodiment, said agent is an antibody. In a preferred embodiment, said agent is an anti-CD11b selected from the group comprising the clone 5C6 and the clone ICRF44. In another preferred embodiment, said agent is an anti-CD18 antibody selected from the group comprising erlizumab and the clone L130.

In another particular embodiment, said agent is a small molecule.

In one embodiment, the inflammation of the invention is associated with monocytes phagocytes accumulation. In one embodiment, said inflammation associated with monocytes phagocytes accumulation is selected from the group comprising retinal inflammation, neurodegenerative diseases, and metabolic disorders.

In one embodiment, said inflammation associated with monocytes phagocytes accumulation is a retinal inflammation. In a particular embodiment, said inflammation is age-related macular degeneration.

In one embodiment, the agent of the invention is administered topically to said subject.

Another object of the invention is a pharmaceutical composition comprising an agent inhibiting the binding of Complement Factor H to CD11b/CD18 and at least one pharmaceutically acceptable excipient.

A further object of the invention is a medicament comprising an agent inhibiting the binding of Complement Factor H to CD11b/CD18.

In one embodiment, the pharmaceutical composition or the medicament of the invention are for use for treating inflammation, preferably age-related macular degeneration.

The present invention further relates to a kit comprising the agent, the pharmaceutical composition, or the medicament as described hereinabove.

Definitions

In the present invention, the following terms have the following meanings:

The term "peptide" refers to a linear polymer of amino acids of less than 50 amino acids linked together by peptide bonds The term "polypeptide" is used in its conventional meaning, i.e., as a sequence of less than 100 amino acids. In one embodiment, a polypeptide of the invention has from 10 to 100 amino acids, preferably from 50 to 100 amino acids. A polypeptide usually refers to a monomeric entity. The term "protein" refers to a sequence of more than 100 amino acids and/or to a multimeric entity. The proteins of the invention are not limited to a specific length of the product. This term does not refer to or exclude post-expression modifications of the protein, for example, glycosylation, acetylation, phosphorylation and the like, as well as other modifications known in the art, both naturally occurring and non-naturally occurring. A protein may be an entire protein, or a subsequence thereof. Particular proteins of interest in the context of this invention are amino acid subsequences comprising CDRs and being capable of binding an antigen. An "isolated protein" is one that has been identified and separated and/or recovered from a component of its natural environment. In preferred embodiments, the isolated protein will be purified (1) to greater than 80, 85, 90, 95% by weight of protein as determined by the Lowry method, and most preferably more than 96, 97, 98, or 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining. Isolated protein includes the protein in situ within recombinant cells since at least one component of the protein's natural environment will not be present. Ordinarily, however, isolated protein will be prepared by at least one purification step.

The term "immunoglobulin" includes a polypeptide having a combination of two heavy and two light chains whether or not it possesses any relevant specific immunoreactivity. The term "antibodies" refers to such assemblies which have significant known specific immunoreactive activity to an antigen of interest (e.g. CFH, CD11b or CD18). The term "CFH, CD11b or CD18 antibodies" is used herein to refer to antibodies which exhibit immunological specificity for CFH, CD11b or CD18 protein. In addition, it also does not exclude antibodies recognizing an epitope spanning CFH protein residues and CD11b or CD18 protein residues, or an epitope spanning CD11b protein residues and CD18 protein residues. Antibodies and immunoglobulins comprise light and heavy chains, with or without an interchain covalent linkage between them. Basic immunoglobulin structures in vertebrate systems are relatively well understood. The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000 Daltons. The four chains are joined by disulfide bonds in a "Y" configuration wherein the light chains bracket the heavy chains starting at the mouth of the "Y" and continuing through the variable region. The light chains of an antibody are classified as either kappa or lambda ([κ], [λ]). Each heavy chain class may be bonded with either a kappa or lambda light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementarity determining regions (CDRs) on each of the VH and VL chains.

The term "binding site" comprises a region of a polypeptide which is responsible for selectively binding to a target antigen of interest (e.g. CFH, CD11b or CD18). Binding domains or binding regions comprise at least one binding site. Exemplary binding domains include an antibody variable domain. The antibody molecules of the invention may comprise a single antigen binding site or multiple (e.g., two, three or four) antigen binding sites.

The term "derived from", before a designated protein (e.g. a CFH, CD11b or CD18 antibody or antigen-binding fragment thereof), refers to the origin of the polypeptide. In an embodiment, the polypeptide or amino acid sequence which is derived from a particular starting polypeptide is a CDR sequence or sequence related thereto. In an embodiment, the amino acid sequence which is derived from a particular starting polypeptide is not contiguous. For example, in an embodiment, one, two, three, four, five, or six CDRs are derived from a starting antibody. In an embodiment, the polypeptide or amino acid sequence which is derived from a particular starting polypeptide or amino acid sequence has an amino acid sequence that is essentially identical to that of the starting sequence, or a region thereof wherein the region consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence.

The term "diabodies" refers to small antibody fragments prepared by constructing sFv fragments (see sFv paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO93/11161; and Holliger et al., Proc. Natl. Acad. Sci., 90:6444-6448 (1993).

The term "peptibodies" refers to biologically active peptides grafted onto an Fc domain. In one embodiment, peptibodies retain some desirable features of antibodies, notably an increased apparent affinity through the avidity conferred by the dimerization of two Fcs.

The term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

The term "epitope" refers to a specific arrangement of amino acids located on a peptide or protein or proteins to which an agent (e.g. an antibody or a small molecule) binds. Epitopes often consist of a chemically active surface grouping of molecules such as amino acids or sugar side chains, and have specific three dimensional structural characteristics as well as specific charge characteristics. Epitopes can be linear or conformational, i.e., involving two or more sequences of amino acids in various regions of the antigen that may not necessarily be contiguous.

The term "fragment" refers to a part or region of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to CFH, CD11b or CD18). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, diabodies or any antigen-binding molecule formed by combination, assembly or conjugation of such antigen binding fragments. Fragments can be obtained, e.g., via chemical or enzymatic treatment of an intact or complete antibody or antibody chain or by recombinant means.

The term "Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "immunospecific", "specific for" or to "specifically bind": as used herein, an antibody is said to be "immunospecific", "specific for" or to "specifically bind" an antigen if it reacts at a detectable level with the antigen, preferably with an affinity constant, Ka, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$, or greater than or equal to $10^9$ $M^{-1}$, or greater than or equal to $10^{10}$ $M^{-1}$. Affinity of an antibody for its cognate antigen is also commonly expressed as a dissociation constant Kd, and in certain embodiments, an antibody specifically binds to antigen if it binds with a Kd of less than or equal to $10^{-4}$ M, less than or equal to about $10^{-5}$ M, less than or equal to about $10^{-6}$ M, less than or equal to $10^{-7}$ M, or less than or equal to $10^{-8}$ M, or less than or equal to $5.10^{-9}$ M, or less than or equal to $10^{-9}$ M, or less than or equal to $5.10^{-10}$ M, or less than or equal to $10^{-10}$ M. Affinities of antibodies can be readily determined using conventional techniques, for example, those described by Scatchard G et al. (Ann NY Acad Sci. 1949, 51:660-672). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

The term "mammal" refers to any mammal, including humans, domestic and farm animals, and zoo, sports, or pet animals, such as dogs, cats, cattle, horses, sheep, pigs, goats, rabbits, etc. Preferably, the mammal is human.

The term "monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "polyclonal antibody" refers to a collection of immunoglobulin molecules that react against a specific antigen, each identifying a different epitope. Thus, contrary to monoclonal antibodies, polyclonal antibodies are not derived from a single cell line.

The term "specificity" refers to the ability to specifically bind (e.g., immunoreact with) a given target, e.g., CFH, CD11b or CD18. A polypeptide may be monospecific and contain one or more binding sites which specifically bind a target, or a polypeptide may be multispecific and contain two or more binding sites which specifically bind the same or different targets. In an embodiment, an antibody of the invention is specific for more than one target. For example, in an embodiment, a multispecific binding molecule of the invention binds to CFH and to CD11b or CD18.

The term "synthetic" with respect to polypeptides includes polypeptides which comprise an amino acid sequence that is not naturally occurring. For example, non-naturally occurring polypeptides are modified forms of naturally occurring polypeptides (e.g., comprising a mutation such as an addition, substitution or deletion) or polypeptides which comprise a first amino acid sequence (which may or may not be naturally occurring) that is linked in a linear sequence of amino acids to a second amino acid sequence (which may or may not be naturally occurring) to which it is not naturally linked in nature.

The terms "single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "small molecule" means a low molecular weight molecule that include lipids, monosaccharides, second messengers, other natural products and metabolites. Small molecules are distinct from macromolecules such as proteins.

The term "competitive antagonist" refers to a receptor antagonist that binds to a receptor (e.g. CD11b/CD18) but does not activate the receptor and that competes with natural ligands (e.g. CFH) for receptor binding sites on said receptor. In one embodiment, of the invention, a competitive antagonist is an antagonist of CD11b/CD18, preferably a small molecule that binds to CD11b/CD18 and inhibits the binding of CFH to CD11b/CD18.

The term "allosteric inhibitor" refers to an agent inhibiting a protein or a protein-protein interaction (e.g. the binding of CFH to CD11b/CD18) by binding at a site other than the protein's active site or protein-protein binding site. In one embodiment of the invention, an allosteric inhibitor is an agent, preferably a small molecule, that binds to CFH or to CD11b/CD18 at a site other than the CFH-CD11b/CD18 binding site.

The term "subject" refers to a mammal, preferably a human. In one embodiment, the subject is a man. In another embodiment, the subject is a woman. In one embodiment, a subject may be a "patient", i.e. a warm-blooded animal, more preferably a human, who/which is awaiting the receipt of, or is receiving medical care or was/is/will be the object of a medical procedure, or is monitored for the development of inflammation. In one embodiment, the subject is an adult (for example a subject above the age of 18). In another embodiment, the subject is a child (for example a subject below the age of 18). In one embodiment the agent of the invention is administered to a human patient in need thereof.

The term "therapeutically effective amount" means the level or amount of agent that is aimed at, without causing significant negative or adverse side effects to the target, (1) delaying or preventing the onset of inflammation; (2) slowing down or stopping the progression, aggravation, or deterioration of one or more symptoms of inflammation; (3) bringing about ameliorations of the symptoms of inflammation; (4) reducing the severity or incidence of inflammation; or (5) curing inflammation. A therapeutically effective amount may be administered prior to the onset of inflammation, for a prophylactic or preventive action. Alternatively or additionally, the therapeutically effective amount may be administered after initiation of inflammation, for a therapeutic action or maintenance of a therapeutic action.

The term "treating" or "treatment" or "alleviation" refers to both therapeutic treatment and prophylactic or preventative measures; wherein the object is to prevent or slow down (lessen) inflammation. Those in need of treatment include those already with the disorder as well as those prone to have inflammation or those in whom inflammation is to be prevented. A subject or mammal is successfully "treated" for an infection if, after receiving a therapeutic amount of an agent according to the present invention, the patient shows observable and/or measurable reduction in or absence of one or more of the following: reduction in the number of pathogenic cells; reduction in the percent of total cells that are pathogenic; and/or relief to some extent, of one or more of the symptoms associated with inflammation; reduced morbidity and mortality, and improvement in quality of life issues. The above parameters for assessing successful treatment and improvement in the disease are readily measurable by routine procedures familiar to a physician.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. A pharmaceutically acceptable carrier or excipient refers to a non-toxic solid, semi-solid or liquid filler, diluent, encapsulating material or formulation auxiliary of any type. For human administration, preparations should meet sterility, pyrogenicity, general safety and purity standards as required by FDA Office of Biologics standards.

The term "about" preceding a value means plus or less 10% of said value.

DETAILED DESCRIPTION

Complement factor H is a large macromolecule composed of 20 globular Short Consensus Repeat domains (SCR) (Zipfel et al., Biochem Soc Trans. 2002, 30:971-978) that is best known for its capacity to inhibit complement activation on "self" cell surfaces by binding C3b and inhibiting the formation of C3bBb. However, CFH also plays an important role in antimicrobial activity of neutrophils (Losse, et al., J Immunol. 2010, 184:912-921), the phagocytosis of opsonized cell debris by monocytes (Kang et al., Immunobiology. 2012, 217:455-464), and protects against oxidative stress (Weismann et al., Nature. 2011, 478:76-81). Its SCR7 binds to the integrin CD11b/CD18 (Complement 3 Receptor, Macrophage-1 antigen, Mac-1) on monocytes and neutrophils Losse, et al., J Immunol. 2010, 184:912-921; Kang et al., Immunobiology. 2012, 217:455-464). CFH is secreted by hepatocytes and abundant in plasma, but also strongly expressed by mononuclear phagocytes such as microglial cells and macrophages (Gautier et al., Nat Immunol. 2012, 13:1118-1128) that contribute significantly to the local concentration of CFH in inflamed tissues (Schlaf et al., Molecular immunology. 2001, 38:231-239).

A polymorphism of the SCR7, which leads to the substitution of tyrosine 402 for histidine (Y402H), is strongly associated with age related macular degeneration. This association is found for both clinical forms of late AMD, wet AMD and geographic atrophy (GA). It is also associated with large soft drusen, sizeable deposits of lipoproteinaceous debris under the retinal pigment epithelium (RPE) that are an important risk factor for late AMD (Despriet et al., JAMA. 2006, 296:301-309; Thompson et al., Hum Mol Genet. 2007, 16:2135-2148). These observations suggest that 402H CFH drives a pathomechanism that is already implicated in early disease development.

The integrin CD11b/CD18 (Complement 3 Receptor, Mac-1) is a cell surface receptor found on polymorphonuclear leukocytes (mostly neutrophils), NK cells, and mononuclear phagocytes like macrophages. CD11b/CD18 is a pattern recognition receptor, capable of recognizing and binding to many molecules found on the surfaces of invading bacteria. CD11b/CD18 also recognizes iC3b when bound to the surface of foreign cells.

WO89/041174 discloses antibodies directed against CD11b/CD18 for inhibiting the recruitment of myelomonocytic cells to inflammatory stimuli. DiScipio et al states that the interaction between polymorphonuclear leukocytes and CFH is mediated by CD11b/CD18 (Journal of Immunology; 1998, 160(8):4057-4066).

The inventors here show that CFH is necessary for chronic age-related subretinal MP accumulation in inflammation-prone $Cx3Cr1^{GFP/GFP}$ mice (see Example 1). In acute light-induced subretinal inflammation, the lack of CFH did not affect the initial subretinal MP build-up, but significantly accelerated their elimination in $Cx3Cr1^{GFP/GFP}$ mice (see Example 2). MP CFH expression was responsible for the deceleration, as shown by adoptive transfer experiments of microglial cells (MCs) to the subretinal space, gene replacement of hepatic CFH in light injured $Cx3Cr1^{GFP/GFP}Cfh^{-/-}$ mice (see Example 2). The inventors also show that CFH binds to CD11b/CD18 and that preventing the binding reverses CFHs inhibitory effect on MP elimination on site of inflammation, including non-recruited macrophages that do not cross vascular endothelium (see Examples 2 and 3). The inventors further show that the AMD associated 402H CFH inhibits MP elimination significantly more than the Y402 form (see Example 4).

The inventors thus demonstrate that inhibiting the binding of CFH to CD11b/CD18 accelerates the elimination of macrophages on the site of inflammation, in particular the elimination of subretinal macrophages.

Therefore, the present invention relates to an agent inhibiting the binding of CFH to CD11b/CD18.

In other words, in one embodiment, the agent of the invention inhibits the interaction between CFH and CD11b/CD18.

Methods for assessing the interaction between two proteins or polypeptides are well-known in the art. Examples of methods for assessing the binding of CFH to CD11b/CD18 include, but are not limited to, biochemical methods such as protein affinity chromatography, affinity blotting, coimmunoprecipitation, and cross-linking; and molecular biological methods such as protein probing, the two-hybrid system, and phage display.

In one embodiment, the agent of the invention binds to Complement Factor H. In a particular embodiment, the agent of the invention specifically binds to Complement Factor H. In one embodiment, the agent of the invention binds CFH to at least one binding site to CD11b/CD18.

In another embodiment, the agent of the invention binds to CD11b/CD18. In one embodiment, the agent of the invention binds CD11b/CD18 to at least one binding site to CFH.

In another embodiment, the agent of the invention binds to CD11b. In one embodiment, the agent of the invention specifically binds to CD11b. In one embodiment, the agent of the invention binds CD11b to at least one binding site to CFH.

In another embodiment, the agent of the invention binds to CD18. In one embodiment, the agent of the invention specifically binds to CD18. In one embodiment, the agent of the invention binds CD18 to at least one binding site to CFH.

In another embodiment, the agent of the invention binds to CD11b and to CD18. In one embodiment, the agent of the invention specifically binds to CD11b and to CD18. In one embodiment, the agent of the invention binds CD11b and CD18 to at least one binding site to CFH.

As used herein, the term "inhibit" means that the agent is capable of blocking, reducing, preventing or neutralizing the binding of CFH to CD11b/CD18.

One skilled in the art can determine the ability of an agent to inhibit the binding of CFH to CD11b/CD18 by measuring for example distance between CFH and CD11b/CD18.

One example of such test is flow cytometry (as shown in Example 3 of the present invention).

In one embodiment, the agent of the invention is a polypeptide or a protein.

In an embodiment, said protein is an antibody molecule selected from the group comprising or consisting of a whole antibody, a humanized antibody, a single chain antibody, a dimeric single chain antibody, a Fv, a Fab, a F(ab)'2, a defucosylated antibody, a bi-specific antibody, a diabody, a triabody, a tetrabody.

In another embodiment, said protein is an antibody fragment selected from the group comprising or consisting of a unibody, a domain antibody, and a nanobody.

In another embodiment, said protein is an antibody mimetic selected from the group comprising or consisting of an affibody, an affilin, an affitin, an adnectin, an atrimer, an evasin, a DARPin, an anticalin, an avimer, a fynomer, a versabody and a duocalin.

In another embodiment, said protein is a peptibody.

A domain antibody is well known in the art and refers to the smallest functional binding units of antibodies, corresponding to the variable regions of either the heavy or light chains of antibodies.

A nanobody is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3).

A unibody is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

An affibody is well known in the art and refers to affinity proteins based on a 58 amino acid residue protein domain, derived from one of the IgG binding domain of staphylococcal protein A.

DARPins (Designed Ankyrin Repeat Proteins) are well known in the art and refer to an antibody mimetic DRP (designed repeat protein) technology developed to exploit the binding abilities of non-antibody polypeptides.

Anticalins are well known in the art and refer to another antibody mimetic technology, wherein the binding specificity is derived from lipocalins. Anticalins may also be formatted as dual targeting protein, called Duocalins.

Avimers are well known in the art and refer to another antibody mimetic technology.

Versabodies are well known in the art and refer to another antibody mimetic technology. They are small proteins of 3-5 kDa with >15% cysteines, which form a high disulfide density scaffold, replacing the hydrophobic core the typical proteins have.

In another embodiment, said protein is an immunoconjugate comprising an antibody or fragment thereof conjugated to a therapeutic agent.

In one embodiment, the protein of the invention is an anti-CFH antibody or antigen binding fragment thereof that inhibits the binding of CFH to CD11b/CD18. Examples of anti-CFH (or anti-Factor H) antibodies include, but are not limited to, antibodies specific for Y402 CFH form, antibodies specific for H402 CFH form (as described in Hakobyan et al., Kidney Int. 2010, 78(8):782-8).

In another embodiment, the protein of the invention is an anti-CD11b antibody or antigen binding fragment thereof that inhibits the binding of CFH to CD11b/CD18. Clones 5C6 (Bio-Rad, formerly Abd Serotec, ref MCA711) and ICRF44 (BD Biosciences, ref 557321) are CD11b antibodies which inhibit the binding of CFH to CD1 b. Therefore, in a particular embodiment, the anti-CD11b antibody is selected form the group comprising the clone 5C6 and the clone ICRF44, or mixtures or derivatives thereof. In an embodiment, the invention provides an antibody that binds essentially the same epitope as the 5C6 antibody.

In another embodiment, the protein of the invention is an anti-CD18 antibody or antigen binding fragment thereof that inhibits the binding of CFH to CD11b/CD18. Erlizumab (Genentech-Roche, rhuMAb CD18) and clone L130 (BD Biosciences, ref 556084) are CD18 antibodies which inhibit the binding of CFH to CD18. Therefore, in a particular embodiment, the anti-CD18 antibody is selected from the group comprising erlizumab and the clone L130, or mixtures or derivatives thereof. In an embodiment, the invention provides an antibody that binds essentially the same epitope as the erlizumab antibody.

In an embodiment, said protein is a monoclonal antibody. In another embodiment, said protein is a polyclonal antibody.

In some embodiments of this invention, antibodies inhibiting the binding of CFH to CD11b/CD18 comprising VH and VL domains, or CDRs thereof may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have a fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence. Advantageously, the CH1 domain, hinge region, CH2 domain, CH3 domain and CL domain (and CH4 domain if present) may all have a fully or substantially human amino acid sequence. In the context of the constant region of a humanized or chimeric antibody, or an antibody fragment, the term "substantially human" refers to an amino acid sequence identity of at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required. The presence of a "fully human" hinge region in antibodies inhibiting the binding of CFH to CD11b/CD18 of the invention may be beneficial both to minimize immunogenicity and to optimize stability of the antibody. It is considered that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example, cysteine residue(s) may be introduced in the Fc region, thereby allowing interchain disulfide bond formation in this region. The homodimeric antibody thus generated may have improved effector function. See Caron et al., J. Exp. Med. 176: 1191-1195 (1992) and Shopes, B. J. Immunol. 148:2918-2922 (1992). Alternatively, an antibody inhibiting the binding of CFH to CD11b/CD18 can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, 2010 Nature Reviews: Immunology, 10:301-316, incorporated herein by reference. Variant of antibodies inhibiting the binding of CFH to CD11b/CD18 in which the Fc region is modified by protein engineering, as described herein, may also exhibit an improvement in efficacy (e.g. in therapeutics/diagnostics), as compared to an equivalent antibody (i.e. equivalent antigen-binding properties) without the Fc modification.

According to one embodiment, the antibody of this invention is humanized. "Humanized" forms of antibodies according to this invention are specific chimeric immunoglobulins, immunoglobulin chains or fragments thereof (such as Fv, Fab, Fab', F(ab')2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework (FR) residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a region of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 3, pp. 394 (1992); Verhoeyen et al. Science, 239, pp. 1534; and U.S. Pat. No. 4,816,567, the entire disclosures of which are herein incorporated by reference. Methods for humanizing the antibodies of this invention are well known in the art.

The choice of human variable domains, both light and heavy, to be used in making the humanized antibodies is very important to reduce antigenicity. According to the so-called "best-fit" method, the sequence of the variable domain of an antibody of this invention is screened against the entire library of known human variable-domain sequences. The human sequence that is closed to the mouse sequence is then accepted as the human framework (FR) for the humanized antibody (Sims et al., J. Immunol. 151, pp. 2296 (1993); Chothia and Lesk, J. Mol. Biol. 196, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al. J. Immunol., 151 (1993)).

Another method of making "humanized" monoclonal antibodies is to use a XenoMouse (Abgenix, Fremont, Calif.) as the mouse used for immunization. A XenoMouse is a murine host according to this invention that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al. Nature 362 (1993) 255), or by selection of antibody repertoires using phage display methods. Such techniques are known to the skilled person and can be implemented starting from monoclonal antibodies as disclosed in the present application. Another way to inhibit protein-protein interaction is the use of small molecules as described in Arkin & Wells (Nature Reviews Drug Discovery. 2004, 3:301-317) and Jin et al. (Annu Rev Pharmacol Toxicol. 2014, 54:435-456).

In one embodiment, the agent of the invention is a small molecule.

As used herein, the term "small molecule" means a molecule having a low molecular weight. In one embodiment, the small molecule of the invention has a molecular weight of less than 1 kDa (1000 Da or daltons). In one embodiment, the small molecule of the invention has a molecular weight of less than 900 Da, 800 Da, 700 Da, 600 Da, 500 Da, 400 Da, 300 Da, 250 Da, 200 Da, 150 Da, or 100 Da.

In a particular embodiment, the agent of the invention is a small molecule inhibitor, or small molecule antagonist. Therefore, in one embodiment, the agent of the invention is a small molecule inhibitor of protein-protein interaction, wherein said protein-protein interaction is between CFH and CD11b/CD18. In one embodiment, the small molecule of the invention is a competitive antagonist. In another embodiment, the small molecule of the invention is an allosteric inhibitor.

One object of the present invention is an agent inhibiting CFH and/or the binding of CFH to CD11b/CD18 for use in the treatment of inflammation.

In one embodiment, the agent of the invention is a preventive and/or therapeutic agent. In a particular embodiment, the agent of the invention is a therapeutic agent.

Within the meaning of the invention, by "inflammation", it is meant, as defined in Dorland's Medical Dictionary, "a localized protective response, elicited by injury or destruction of tissues, which serves to destroy, dilute or wall off both the injurious agent and the injured tissue". It is characterized by fenestration of the microvasculature, leakage of the elements of blood into the interstitial spaces, and migration of leukocytes into the inflamed tissue. On a macroscopic level, this is usually accompanied by the familiar clinical signs of erythema, edema, hyperalgesia (tenderness), and pain.

In one embodiment, the agent according to the invention is for use in the treatment of inflammation, wherein said inflammation is selected from the group comprising age-related macular degeneration (AMD), retinitis pigmentosa, Parkinson's disease, multiple sclerosis, Alzheimer's disease, obesity, atherosclerosis, allergies, ankylosing spondylitis, arthritis (osteoarthritis, rheumatoid arthritis, or psoriatic arthritis), asthma, graft versus host disease, Crohn's disease, colitis, dermatitis, diverticulitis, fibromyalgia, hepatitis, irritable bowel syndrome, systemic lupus erythematous, nephritis, and ulcerative colitis.

In one embodiment, the inflammation of the invention is an acute inflammation. In another embodiment, the inflammation of the invention is a chronic inflammation.

In one embodiment, the inflammation of the invention is a nonresolving inflammation. In one embodiment, the inflammation of the invention is a low-grade chronic inflammation. In one embodiment, the inflammation of the invention is a nonresolving and low-grade chronic inflammation.

In one embodiment, the inflammation of the invention is a nonresolving and low-grade chronic inflammation selected from the group comprising metabolic diseases, such as obesity and atherosclerosis; neurodegenerative diseases and cancers.

In one embodiment, the agent of the invention is for use in the treatment of inflammation associated with mononuclear phagocyte accumulation.

Mononuclear phagocytes (MPs) comprise a family of cells that include microglial cells (MCs), monocytes (Mos) and macrophages (MTps). Inflammation associated with mononuclear phagocytes accumulation includes, but is not limited to, retinal inflammation, such as age-related macular degeneration (AMD) or retinitis pigmentosa; neurodegenerative diseases, such as Parkinson's disease, multiple sclerosis or Alzheimer's disease; metabolic disorders, such as obesity or atherosclerosis; allergies; ankylosing spondylitis; arthritis, such as osteoarthritis, rheumatoid arthritis, or psoriatic arthritis; asthma, graft versus host disease; Crohn's disease; colitis; dermatitis; diverticulitis; fibromyalgia; hepatitis; irritable bowel syndrome; systemic lupus erythematous; nephritis; and ulcerative colitis.

In one embodiment, the inflammation according to the invention is selected from the group comprising retinal inflammation, such as age-related macular degeneration (AMD) or retinitis pigmentosa; neurodegenerative diseases, such as Parkinson's disease, multiple sclerosis or Alzheimer's disease; metabolic disorders, such as obesity or atherosclerosis.

In one embodiment, the inflammation according to the invention is an ophthalmic inflammation.

In one preferred embodiment, the inflammation according to the invention is a retinal inflammation. Within the meaning of the invention, by "retinal inflammation", it is meant an inflammation of the subretinal space mediated by mononuclear phagocytes. In an embodiment, the inflammation according to the invention is a subretinal inflammation.

In an embodiment, the retinal inflammation of the invention comprises age-related macular degeneration (AMD) and retinitis pigmentosa.

In one embodiment, the agent of the invention is for use in the treatment of age-related macular degeneration. In a particular embodiment, the age-related macular degeneration comprises early AMD, atrophic AMD and neovascular (or wet) AMD. In one embodiment, the agent of the invention is for use in the treatment of atrophic AMD. In another embodiment, the preventive and/or therapeutic agent of the invention is for use in the treatment of neovascular AMD.

In one embodiment, the AMD according to the invention is at an early stage. Early stage is characterized by accumulation in and around the macula of extracellular deposits called drusen, associated with pigmented spots (pigmentary epithelium alterations).

In another embodiment, the AMD according to the invention is at late stage. Late stage is characterized by uni- or bilateral complications. Late sage AMD may be atrophic AMD or wet AMD.

In one embodiment, the subject is affected by inflammation, i.e. an inflammation associated with mononuclear phagocytes accumulation. In a particular embodiment, the subject is affected by a retinal inflammation. In a preferred embodiment, the subject is affected by age-related macular degeneration (AMD).

In one embodiment, the AMD is early stage AMD. In another embodiment, the AMD is late stage AMD. In one embodiment, the subject is affected by choroidal neovascularization AMD ("wet" AMD). In another embodiment, the subject is affected by geographic atrophy ("dry" AMD).

In another embodiment, the subject is susceptible to develop inflammation, i.e. to develop mononuclear phagocytes accumulation. In a particular embodiment, the subject is at risk of developing retinal inflammation. In a preferred embodiment, the subject is at risk of developing AMD.

Examples of risks of developing AMD include, but are not limited to, heredity, lifestyle such as smoking, sun exposure or poorly balanced diet, age, excessive blood concentration of cholesterol, high blood pressure, and the like.

In one embodiment, the subject of the invention is elderly. As used herein, the term "elderly" means that the subject is at least 50 years old, at least 55, 60, 65, 70, 75, 80, 85 or 90 years old.

In a particular embodiment, the subject is at risk of developing AMD due to a polymorphism of the SCR7 of CFH, which leads to the substitution of tyrosine 402 for histidine (Y402H).

In one embodiment, the subject has not yet been treated with another treatment for inflammation, preferably AMD. In another embodiment, the subject has already been treated with another treatment for inflammation, preferably AMD.

An object of the invention is a composition comprising at least one of the agent of the invention as described hereinabove.

Another object of the invention is a pharmaceutical composition comprising at least one of the agent of the invention as described hereinabove and at least one pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

The invention further relates to a medicament comprising an agent, a composition or a pharmaceutical composition of the present invention.

In one embodiment, the composition, the pharmaceutical composition or the medicament of the invention is used for treating (or for use in treating) inflammation, preferably AMD.

Preferably, the composition, the pharmaceutical composition or the medicament of the invention comprises a therapeutically effective amount of the agent of the invention.

In one embodiment, the composition, the pharmaceutical composition or the medicament of the invention further comprises an additional preventive and/or therapeutic agent. According to one embodiment, said additional preventive and/or therapeutic agent is another agent for treating inflammation, in particular AMD.

It will be understood that the total daily usage of the agent of the invention, composition, pharmaceutical composition and medicament of the present invention will be decided by the attending physician within the scope of sound medical judgment. The specific therapeutically effective dose level for any particular patient will depend upon a variety of factors including the disorder being treated and the severity of the disorder; activity of the specific agent employed; the specific composition employed, the age, body weight, general health, sex and diet of the patient; the time of administration, route of administration, and rate of excretion of the specific agent employed; the duration of the treatment; drugs used in combination or coincidental with the specific agent employed; and like factors well known in the medical arts. For example, it is well within the skill of the art to start doses of the agent at levels lower than those required to achieve the desired therapeutic effect and to gradually increase the dosage until the desired effect is achieved. However, the daily dosage of the products may be varied over a wide range from about 10 to about 10000 mg per adult per day, preferably 100 to about 5000, more preferably from about 200 to about 2000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10000 mg of the active ingredient, preferably 5 to about 5000, more preferably from about 10 to about 2000 mg of the active ingredient. An effective amount of the drug is ordinarily supplied at a dosage level from 0.01 mg/kg to about 100 mg/kg of body weight per day, preferably from about 0.05 mg/kg to 40 mg/kg of body weight per day, more preferably from about 0.1 mg/kg to 20 mg/kg of body weight per day, more preferably from about 0.2 mg/kg to 1 mg/kg of body weight per day.

Schedules and dosages for administration of the antibody in the pharmaceutical compositions of the present invention can be determined in accordance with known methods for these products, for example using the manufacturers' instructions. For example, an antibody present in a pharmaceutical composition of this invention can be supplied at a concentration of 10 mg/mL in either 100 mg (10 mL) or 500 mg (50 mL) single-use vials. The product is formulated for intravenous (IV) administration in 9.0 mg/mL sodium chloride, 7.35 mg/mL sodium citrate dihydrate, 0.7 in g/mL polysorbate 80, and Sterile Water for Injection. The pH is adjusted to 6.5. It will be appreciated that these schedules are exemplary and that an optimal schedule and regimen can be adapted taking into account the affinity and tolerability of the particular antibody in the pharmaceutical composition that must be determined in clinical trials.

For use in administration to a subject, the composition will be formulated for administration to the subject. The compositions of the present invention may be administered orally, parenterally, topically, by inhalation spray, rectally, nasally, buccally, vaginally or via an implanted reservoir. The term administration used herein includes subcutaneous, intravenous, intramuscular, intraocular, intra-articular, intrasynovial, intrastemal, intrathecal, intrahepatic, intralesional and intracranial injection or infusion techniques.

In one embodiment, the composition, pharmaceutical composition, medicament of the invention is in a form adapted for topical administration.

Examples of forms adapted for topical administration include, but are not limited to, liquid, paste or solid compositions, and more particularly in form of aqueous solutions, drops, eye drops, ophthalmic solutions, dispersions, sprays, microcapsules, micro- or nanoparticles, polymeric patch, or controlled-release patch.

In one embodiment, the composition, pharmaceutical composition, or medicament of the invention comprises one or more pharmaceutical acceptable carrier for a formulation adapted for topical administration, more particularly for topical ocular administration.

In one embodiment, the composition, pharmaceutical composition, or medicament of the invention is in a form adapted for injection, such as, for example, for intraocular, intramuscular, subcutaneous, intradermal, transdermal or intravenous injection or infusion.

Examples of forms adapted for injection include, but are not limited to, solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In a particular embodiment, the composition, pharmaceutical composition, or medicament of the invention is in a form adapted for intraocular administration, more preferably for intraocular injection.

Within the meaning of the invention, by "intraocular administration" it is meant an injection of the agent directly in the interior of the eye, wherein the interior of the eye means any area located within the eyeball, and which generally includes, but is not limited to, any functional (e.g. for vision) or structural tissues found within the eyeball, or tissues or cellular layers that partially or completely line the interior of the eyeball. Specific examples of such areas include the anterior chamber, the posterior chamber, the vitreous cavity, the choroid, the macula, and the retina, and blood vessels and nerves which vascularize or innervate a posterior ocular region or site. In one embodiment, interior of the eye means the posterior segment of the eye, including the posterior chamber, the vitreous cavity, the choroid, the macula, and the retina, and blood vessels and nerves which vascularize or innervate a posterior ocular region or site. According to this embodiment, the intraocular administration refers to an administration within the posterior segment of the eye, preferably within the vitreous, and the intraocular administration is preferably an intravitreal injection.

In one embodiment, the composition, pharmaceutical composition, or medicament of the invention is administered to the subject in need thereof at least once a day. For example, the composition, pharmaceutical composition, or medicament of the invention may be administered once a day, twice a day, or three times a day. In a preferred embodiment, the composition, pharmaceutical composition, or medicament of the invention is administered to the subject in need thereof once a day.

In another embodiment, the composition, pharmaceutical composition, or medicament of the invention is administered to the subject in need thereof at least once a week. For example, the composition, pharmaceutical composition, or medicament of the invention may be administered once a week, twice a week, three times a week, four times a week or up to seven times a week.

In another embodiment, the composition, pharmaceutical composition, or medicament of the invention is administered to the subject in need thereof once a month, two times a month, every two months, every two or three month, two times a year or once a year.

Another object of the invention is a method of treating inflammation in a subject in need thereof, comprising administering to said subject a therapeutically effective amount of the agent of the invention.

In one embodiment, the method of the invention is for treating inflammation associated with mononuclear phagocytes accumulation. In a preferred embodiment, the method of the invention is for treating age-related macular degeneration.

In one embodiment, the composition, pharmaceutical composition or medicament of the invention is administered to the subject.

Another object of the present invention is a method for inhibiting CFH activity in a subject in need thereof, comprising administering to the subject an effective amount of the agent of the invention.

The present invention also relates to a method for inhibiting CFH binding to CD11b/CD18 in a subject in need thereof, comprising administering to the subject an effective amount of the agent of the invention.

Another object of the present invention is a method of eliminating mononuclear phagocytes accumulation in a subject in need thereof comprising administering to said subject a therapeutically effective amount of the agent as described hereinabove.

In one embodiment, the method of the invention is for eliminating mononuclear phagocytes accumulation, thereby treating inflammation associated with mononuclear phagocytes accumulation in a subject in need thereof, comprising administering to said subject a therapeutically effective amount of the agent as described hereinabove.

A further object of the present invention is a method for accelerating the elimination of macrophages on the site of inflammation in a subject in need thereof comprising administering to said subject a therapeutically effective amount of the agent as described hereinabove.

In one embodiment, macrophages include non-recruited tissue macrophages, i.e. macrophages that are into the bloodstream.

The present invention also relates to a kit comprising an agent, a pharmaceutical composition or a medicament according to the invention.

In one embodiment, the kit of the invention further comprises means to administer the agent, the pharmaceutical composition or the medicament to a subject in need thereof.

In one embodiment, the kit of the invention further comprises instructions for the administration of the agent, the pharmaceutical composition or the medicament to said subject.

In one embodiment, the kit of the invention comprises two parts wherein the first part comprises the agent, pharmaceutical composition or medicament according to the invention, and wherein the second part comprises an additional preventive and/or therapeutic agent. According to one embodiment, said additional preventive and/or therapeutic agent is another agent for treating inflammation, in particular AMD.

In one embodiment, the kit of the invention is used for treating (or for use in treating) inflammation.

In one embodiment, the part of the kit of part comprising the additional preventive and/or therapeutic agent is in a form adapted to the same administration route than the agent, pharmaceutical composition or medicament of the invention. In another embodiment, the part of the kit of part comprising the additional preventive and/or therapeutic agent is in a form adapted to another administration route than the agent, pharmaceutical composition or medicament of the invention.

BRIEF DESCRIPTION OF THE DRAWINGS

FIG. 1 is a set of graphs showing that CFH deficiency prevents chronic pathogenic subretinal inflammation. A: Representative images of 12 month-old IBA-1stained RPE-flatmounts of Cx3cr1$^{GFP/GFP}$ and Cx3cr1$^{GFP/GFP}$cfh$^{-/-}$ mice and quantification of subretinal IBA-1$^+$ MPs in 2-3-month-old and 12-month-old mice of the indicated strains (n=11-17 per group, one-way Anova/Bonferroni test *p<0.0001 versus all other groups, $^\$$p<0.0001 versus Cx3cr1$^{GFP/GFP}$ 12-month-old). B: Micrographs, taken 1000 µm from the optic nerve of 12-month-old Cx3cr1$^{GFP/GFP}$ and Cx3cr1$^{GFP/GFP}$Cfh$^{-/-}$ mice. B': Photoreceptor nuclei rows at increasing distances (−3000 µm: inferior pole, +3000 µm: superior pole) from the optic nerve (0 µm) in 12-month-old mice. B": Quantification of the area under the curve of photoreceptor nuclei row counts of 12-month-old indicated transgenic mouse strains (one-way Anova/Bonferroni test C''': n=4-6/group, *p<0.001; D: n=7-9/group *p<0.001). Mice were taken from several (≥3) independent cages for the quantifications. ONL: outer nuclear layer. Scale bar=50 μm. C: Micrographs, taken in the superior periphery of peanut agglutinin (staining cone segments, red), cone arrestin (white), IBA-1 (green) triple stained 12 month-old Cx3cr1GFP/GFP and Cx3cr1GFP/GFP Cfh−/− mice. C': Cone density quantifications on retinal flatmounts in peripheral and central, inferior and superior retina (−3000 μm: inferior pole, +3000 μm: superior pole, optic nerve: 0 μm) and their average (C''') in 12 month-old mice of the indicated transgenic mouse strains. (C''': one-way Anova/Bonferroni test: *p<0.0001 versus all other groups; Mann Whitney $p=0.0024 versus Cx3cr1GFP/GFP mice). N is the number of replicates indicated in the graphs; replicates represent quantifications of eyes from different mice of at least three different cages.

EXAMPLES

Figure 2:
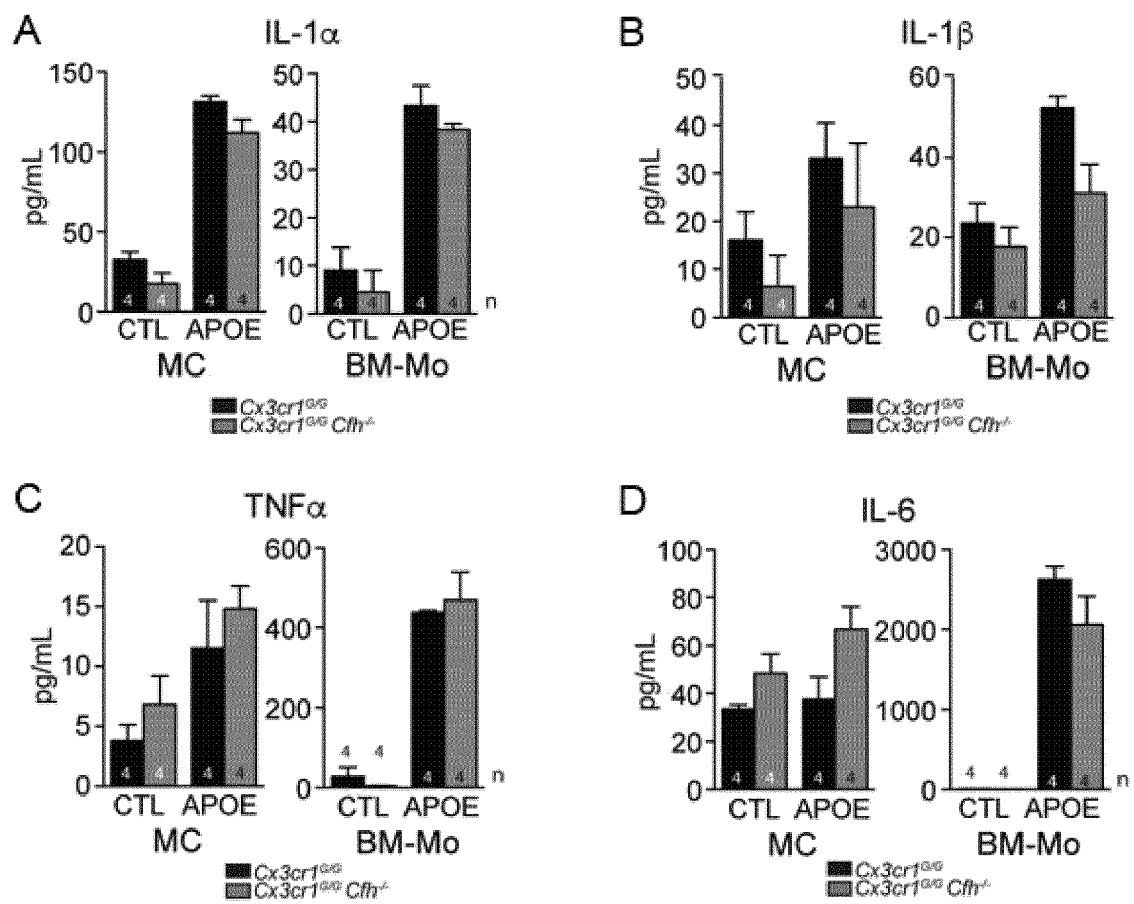
FIG. 2 is a set of graphs showing cytokine multiplex analysis (A: IL-1α; B: IL-1β; C: TNFα; D: IL-6) of supernatants from cultured primary bone marrow monocytes (BM-Mos, 100 000 cells/well) and brain microglial cells (MCs, 200 000 cells/well), incubated for 24 h in serum free DMEM medium or stimulated with APOE3 (5 μg/ml) of Cx3cr1$^{GFP/GFP}$ and Cx3cr1$^{GFP/GFP}$ Cfh$^{-/-}$ mice.

The present invention will be better understood with reference to the following examples. These examples are intended to representative of specific embodiments of the invention, and are not intended as limiting the scope of the invention.

Materials and Methods

Animals

Cfh$^{-/-}$-mice were a generous gift. Cx3cr1$^{GFP/GFP}$-mice were purchased (Charles River Laboratories, Jackson laboratories) and Cx3Cr1$^{GFP/GFP}$Cfh$^{-/-}$ mouse strains were generated. All mice were either negative or backcrossed to become negative for the Crb1$^{rd8}$, Pde6b$^{rd1}$, and Gnat2$^{cpfl3}$ mutations. Mice were housed in the animal facility under specific pathogen-free condition, in a 12/12h light/dark (100-500 lux) cycle with water and normal diet food available ad libitum. All experimental protocols and procedures were approved by the local animal care ethics committee "Comité d'éthique en experimentation animale Charles Darwin" (No Ce5/2010/011, Ce5/2010/044, Ce5/2011/033).

Choroidal and Retinal Flatmounts for Mononuclear Phagocytes and Cones Quantification Eyes were enucleated, fixed in 4% PFA 30 minutes and sectioned at the limbus; the cornea and lens were discarded. The retinas were carefully peeled from the RPE/choroid/sclera. Retina and choroid were incubated with Peanut agglutinin Alexa 594 (Thermofisher; 1:50), anti-IBA-1 antibody (Wako chemicals; 1:400), and anti-mouse cone-arrestin antibody (Millipore, #AB15282; 1:10 000) followed by secondary anti-rabbit antibody coupled to Alexa 488 and Alexa 647 (Thermo Fisher; 1:500) and nuclear staining using Hoechst. Choroids and retinas were flatmounted and viewed with a fluorescence microscope DM5500B (Leica). IBA-1+ cells were counted on whole RPE/choroidal flatmounts and on the outer segment side of the retina. PA+cone arrestin+ cells were counted on oriented retinal flatmounts in the central and peripheral retina.

Histology and Immunohistochemistry

Eyes were fixed in 0.5% glutaraldehyde, 4% PFA for 2h, dehydrated and mounted in Historesin (Leica). 5 µm oriented sections crossing inferior pole, optic nerve and superior pole were cut and stained with toluidin blue. Rows of nuclei in the ONL were counted at different distances from the optic nerve (Sennlaub et al., EMBO Mol Med. 2013, 5: 1775-1793). For immunohistochemistry, eyes from 4d light-challenged mice were fixed for 2h in 4% PFA, incubated in 30% sucrose overnight at 4° C., embedded in OCT and sectioned (10 µm), and stained with anti-C3 antibody (clone 11H9 Hycult biotech; 1:50), anti-C3b/iC3b/C3c antibody (clone 3/26 Hycult biotech; 1:50), and anti-CFH antibody (ab8842 Abcam; 1:100) and appropriate secondary antibodies and Hoechst nuclear stain.

Light Challenge Model

Two- to three-month-old mice were adapted to darkness for 6 hours, pupils dilated daily and exposed to green LED light (starting at 2 AM, 4500 Lux, JP Vezon equipements) for 4 days and subsequently kept in cyclic 12h/12h normal facility conditions as previously described (Sennlaub et al, EMBO Mol Med. 2013, 5:1775-1793). MP count was assessed at the end of light exposure or 10 (d14) later.

Hydrodynamic Injection

Murine Complement Factor H was cloned in Plive vector (Mirus) using NheI and SacII restriction sites. The plasmid was sequenced and amplified with endotoxin-free Megaprep kits (Qiagen). 100 µg of plasmids were injected per mouse diluted in NaCl 0.9%. The volume injected in the venous tail was 10% of the body weight (around 25 g) (Rayes et al., Blood. 2010, 115:4870-4877). Four days later, mice were exposed to the light challenge model and 50 µl of blood were taken (mandibular vein) at D0, D4 and D14 to quantify C3 concentration.

Reverse Transcription and Real-Time Polymerase Chain Reaction and ELISA

RT-PCRs (CFH sense: 5'AAG AGA TTC ACC GCC ATT TC-3'; CFH antisense: 5'TGC ATG TGC CTT TCT AAA CA 3'; S26 sense: 5'AAG TTT GTC ATT CGG AAC ATT-3'; S26 antisense: 5'AGCAGGTCTGAATCGTGG TG-3') using Sybr Green (Life Technologies) and ELISAs on isolated plasma using mouse C3 ELISA kit (Innovative Research) as previously described (Sennlaub et al., EMBO Mol Med. 2013, 5:1775-1793).

Monocyte and Microglial Cell Preparations, Analysis, and Culture

Blood samples were collected for determination of plasma C3 (Innovative Research) levels by ELISA. Bone marrow monocytes, circulating monocytes, central nervous MC and retinal MC were purified. Mos were isolated by negative selection (EasySep Mouse Enrichment Kit, Stemcell Technologies). MCs were prepared from dissociated PBS-perfused brains or retinas (Neural Dissociation Kit, Miltenyi Biotec). After dissociation, 70 µm filtered cell suspensions were washed and myelin was eliminated Percoll density gradient centrifugation. Then cells labeled with anti-CD11b microbeads (clone M1/70.15.11.5, Miltenyi Biotec) were purified by MS Columns (Miltenyi Biotec) and washed. No serum was used in any step of the purification to avoid cell contamination with serum derived CFH. The cells were used for adoptive transfer experiments, analyzed by RT-qPCR or cultured for 24h in serum free DMEM, in presence of recombinant human APOE3 (Interchim; 10 µg/mL), and finally their supernatants were analyzed by cytokine multiplex array (MILLIPLEX MAP Mouse Cytokine/Chemokine Magnetic Bead Panel, Merck Millipore).

Subretinal Adoptive MP Transfer and Clearance

According to Levy et al. (EMBO Mol Med. 2015, 7:211-226), brain microglia of the indicated mouse strains were sorted as describe above, labeled in 10 µM CFSE (Life Technologies), washed and resuspended in PBS. 12000 cells (4 µL) were injected using glass microcapillaries (Eppendorf) and a microinjector in the subretinal space of anesthetized 10-14 weeks old wildtype or Cfh$^{-/-}$-mice. A hole was pierced with the glass capillary prior to the subretinal injection to avoid intra-ocular pressure increase and to allow retinal detachment with 4 µl of solution. The subretinal injection was verified by fundoscopy. In specific experiments, cells were co-injected with human CFH (500 µg/ml) from donors (Tecomedical), purified 402H and 402Y CFH (Claire Harris) or synthetized (LFB Biotechnologies, Lille), anti-CD11b (10 µg/ml, clone 5C6 Abd Serotec), anti-C3b/iC3b/C3c antibody (10 µg/ml, clone 3/26 Hycult biotech), isotype control rat IgG2b (10 µg/ml, Invivogen), and isotype control mouse IgM (10 µg/ml, Invivogen). Eyes were enucleated after 24 hours, fixed in PFA 4% 30 minutes and labeled with DAPI. Eyes with hemorrhages were discarded. CFSE+ cells in the subretinal space were quantified on flatmounts on the RPE side of the retina and on the apical side of the RPE.

CFH Binding Assay by Flow Cytometry

Figure 6:
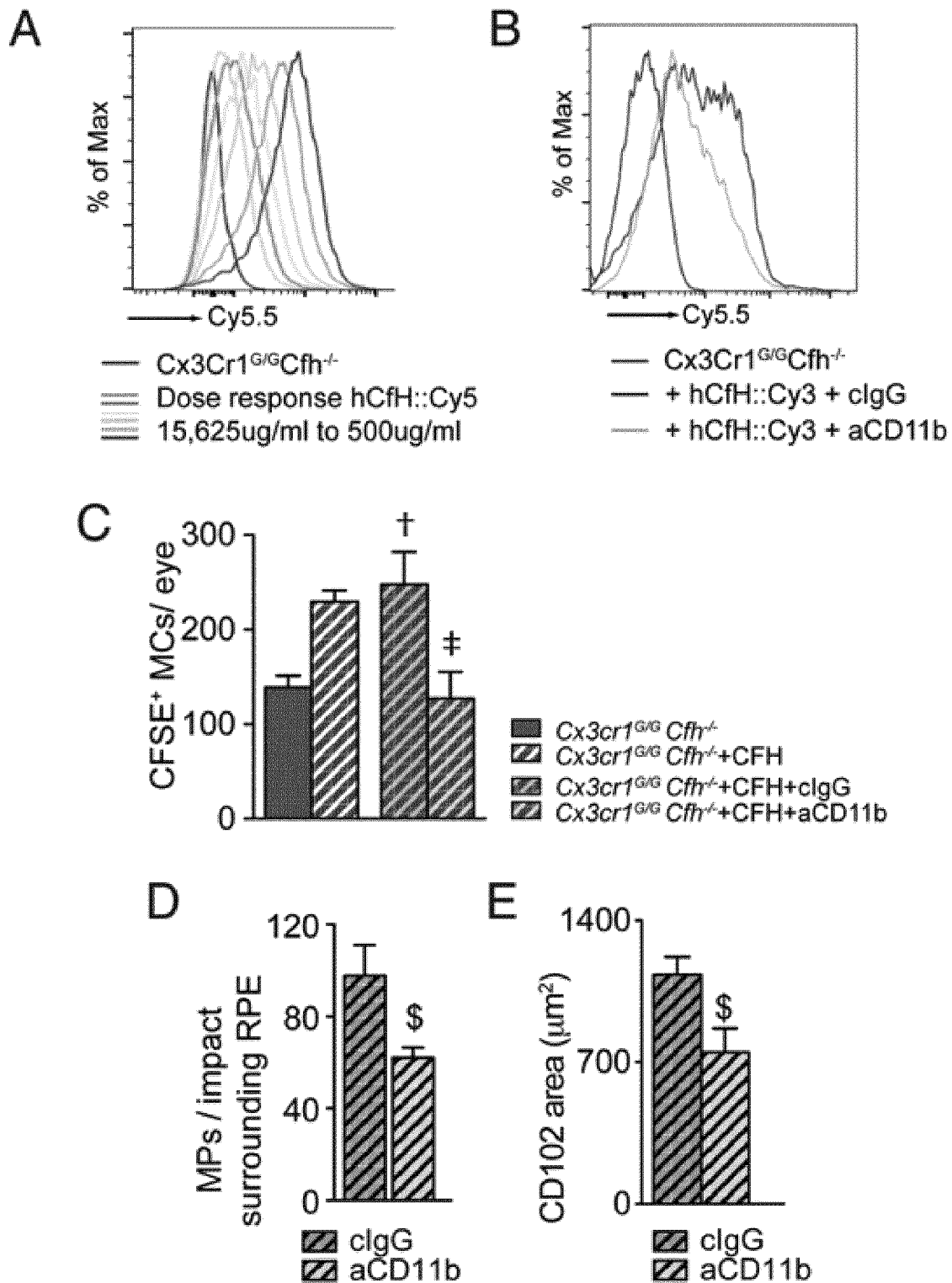
FIG. 6 is a set of graphs showing that CFH fixation to CD11b/CD18 inhibits MP elimination. A and B: Representative cytometry images of (A) sorted brain Cx3cr1$^{GFP/GFP}$Cfh$^{-/-}$ Microglial Cells (gated on GFP$^{high}$) incubated with increasing dose of hCFH::Cy5.5 (15,625 μg/ml to 500 gig/ml), and (B) sorted Cx3cr1$^{GFP/GFP}$Cfh$^{-/-}$ bone marrow monocytes pre-incubated with an isotype or anti-CD11b 5C6 antibody before hCFH::cy3 (100 μg/ml) or PBS incubation. Bone marrow monocytes were gated on GFP+ CD115+ LY6G− cells (The experiments were repeated three times with similar results). C: Quantification of Cx3cr1$^{GFP/GFP}$Cfh$^{-/-}$ CFSE+ MCs with control IgG or anti-CD11b 5C6 antibody, 24h after adoptive transfer (n=12-13/group; Anova/Bonferroni test †p<0.0001 versus Cx3cr1$^{GFP/GFP}$Cfh$^{-/-}$ CFSE+ MCs, ‡p<0.0001 versus Cx3cr1$^{GFP/GFP}$Cfh$^{-/-}$+CFH+cIgG). Scale bar=50 μm. D: Quantification of subretinal IBA-1+ MPs on the RPE counted at a distance of 0-500 μm to CD102+CNV 7 days after the laser-injury of 3-month-old Cx3cr1$^{GFP/GFP}$ mice injected with control IgG, or anti CD11b 5C6 at d0 (n=7-12/group MannWhitney $p=0.0298 versus cIgG). E: Quantification of CD102+CNV on the RPE/choroid at 7 days after the laser-injury of 3-month-old Cx3cr1$^{GFP/GFP}$ mice injected with control IgG, or anti CD11b 5C6 at d0 (n=7-12/group MannWhitney $p=0.035 versus cIgG).

Human CFH was conjugated to Cyanin 5.5 (Abcam conjugation kits). MCs from Cx3Cr1$^{GFP/GFP}$Cfh$^{-/-}$ were stained 30 minutes with conjugated human CFH of the indicated concentrations (with or without preincubation of IgG and anti CD11b 10 µg/ml) in PBS at 37° C. and washed two times before acquisition on a BD Fortessa flow cytometer (BD biosciences). Analysis was performed using Flowjo. Briefly, doublets were eliminated with FSC-H, FSC-W, SSC-H and SSC-W and microglial cells were analyzing as GFP$^{high}$ cells. Bone marrow monocytes incubated with hCFH::Cy5, were labeled with rat anti-CD115-PE (Abd Serotec), rat anti-LY6G AlexaFluor 700 (BD Biosciences) to be defined as GFP$^+$, CD115$^+$, LY6G$^-$ cells. Note that the anti-CD11b clone M1/70.15.11.5 used for MC purification does not interfere with CFH binding as shown in FIG. 6A and the fact that recombinant CFH is capable to reverse the accelerated elimination of Cx3cr1$^{GFP/GFP}$ Cfh$^{-/-}$ MCs and TRE2Cfh-/- MCs sorted using clone M1/70 (FIG.

3). This difference is likely due to the fact clone M1/70 recognizes a distinct epitope of CD11b compared to the 5C6 clone (Rosen and Gordon, J Exp Med. 1987, 166, 1685-1701).

Laser-Injury Model

Laser-coagulations were performed with a 532 nm ophtalmological laser mounted on an operating microscope (Vitra Laser, 532 nm, 450 mW, 50 ms, and 250 µm). Intravitreal injections of 2 µl of PBS, isotype control rat IgG2b (50 µg/ml, Invivogen), or rat anti-mouse CD11b (50 µg/ml, clone 5C6 Abd Serotec) were performed using glass capillaries (Eppendorf) and a microinjector, and mice were sacrificed at day 10. RPE and retinal flatmounts were stained and quantified as previously described (Sennlaub et al., EMBO Mol Med. 2013, 5, 1775-1793) using polyclonal rabbit anti-IBA-1 (Wako) and rat anti-mouse CD102 (clone 3C4, BD Biosciences) appropriate secondary antibodies and counterstained with Hoechst if indicated. Preparations were observed under a fluorescence microscope (DM5500, Leica) and IBA-1+ MPs on the RPE were counted in a diameter of 500 µm around the CD102+ neovascularizations.

Statistical Analysis

Sample sizes for experiments were determined according to previous studies (Combadiere et al., J Clin Invest. 2007, 117, 2920-2928; Sennlaub et al., EMBO Mol Med. 2013, 5, 1775-1793). Severe hemorrhage secondary to subretinal injection interferes with MP clearance and was used as exclusion criteria. Graph Pad 6 (GraphPad Software) was used for data analysis and graphic representation. All values are reported as mean+/−SEM. Statistical analysis was performed by one-way ANOVA followed by Bonferroni post-test (for multiple comparison) or Mann-Whitney U-test (2-group comparison) among means depending on the experimental design. The n- and P-values are indicated in the figure legends.

Example 1: CFH Deficiency Prevents Chronic Pathogenic Subretinal Inflammation

The subretinal space does not contain significant numbers of mononuclear phagocytes (MPs) under normal conditions. This is likely the result of physiologically low levels of chemoattractants along with strong immunosuppressive RPE signals that quickly eliminate infiltrating MPs (Sennlaub et al, EMBO Mol Med. 2013, 5:1775-1793; Levy et al., EMBO Mol Med. 2015, 7:211-226). $Cx3cr1^{GFP/GFP}$-mice do not develop drusen and RPE atrophy, but do model MP accumulation on the RPE, as well as the associated photoreceptor degeneration and excessive CNV observed in AMD (Combadière et al., J Clin Invest. 2007, 117:2920-2928; Levy et al., EMBO Mol Med. 2015, 7:211-226). To evaluate a potential role of CFH in subretinal MP accumulation, $Cx3cr1^{GFP/GFP}Cfh^{-/-}$-mice were generated. All mice were free of the $Crb1^{rd8}$ contamination, that can lead to AMD like feature, and raised under 12h light/12h dark cycles at 100-500 lux at the cage level, with no additional cover in the cage. Quantification of subretinal IBA-1+ MPs on retinal and RPE/choroidal-flatmounts of 2-3-month and 12-month-old mice revealed that the age-related increase in subretinal MPs in $Cx3cr1^{GFP/GFP}$-mice was nearly completely prevented in $Cx3cr1^{GFP/GFP}Cfh^{-/-}$-mice (FIG. 1 A). We have previously shown that the accumulation of subretinal MPs observed in 12-month-old $Cx3cr1^{GFP/GFP}$-mice is associated with significant photoreceptor degeneration (Sennlaub et al, EMBO Mol Med. 2013, 5:1775-1793). Micrographs, taken at equal distance from the optic nerve of 12-month-old mice also show that the thinning of the outer nuclear layer (ONL that harbors the nuclei of the photoreceptors) observed in $Cx3cr1^{GFP/GFP}$-mice is not observed in $Cx3cr1^{GFP/GFP}Cfh^{-/-}$-mice (FIG. 1B). Photoreceptor nuclei row counts (FIG. 1B') and calculation of the area under the curve (FIG. 1B") showed that $Cx3cr1^{GFP/GFP}Cfh^{-/-}$-mice were significantly protected against the photoreceptor cell loss observed in $Cx3cr1^{GFP/GFP}$-mice and not significantly different to $Cfh^{-/-}$- and wildtype-mice.

Similarly, Cfh deficiency completely protected against cone loss observed on peanut agglutinin/cone arrestin stained retinal flatmounts from 12m-old $Cx3cr1^{GFP/GFP}$ mice (FIGS. 1C, C' and C"). It had no effect on key pathogenic cytokine secretion of MPs in vitro (FIG. 2A-D), suggesting that the numerical increase rather than differences in polarization provokes the degeneration.

Therefore, these results show that CFH significantly contributes to the chronic, age-related subretinal MP accumulation and associated photoreceptor degeneration observed in inflammation-prone $Cx3cr1^{GFP/GFP}$-mice.

Example 2: MP-Derived CFH Inhibits the Resolution of Acute Subretinal Inflammation Next the effect of CFH in an acute light-induced model of subretinal inflammation was evaluated. The intensity of our light-challenge model used herein was calibrated to induce substantial subretinal inflammation in inflammation-prone $Cx3cr1^{GFP/GFP}$-mice but not in C57BL6/J control mice (Sennlaub et al, EMBO Mol Med. 2013, 5:1775-1793). Quantification of subretinal IBA-1+ MPs on retinal and RPE/choroidal-flatmounts after a four-day light-challenge revealed that acute subretinal MP accumulation, observed at 4d, was similar in $Cx3cr1^{GFP/GFP}$- and $Cx3cr1^{GFP/GFP}Cfh^{-/-}$-mice. However, after an additional 10d in normal light conditions the MP accumulation in $Cx3cr1^{GFP/GFP}Cfh^{-/-}$-mice had subsided significantly more quickly than in $Cx3cr1^{GFP/GFP}$-mice (FIG. 3A).

Similarly to $Cfh^{-/-}$ mice (Pickering et al., Nat Genet. 2002, 31:424-428), $Cx3cr1^{GFP/GFP}Cfh^{-/-}$-mice are characterized by low circulating levels of complement factor C3 (FIG. 4A-D), likely due to un-inhibited plasma complement activation and exhaustion, which might interfere with subretinal MP recruitment. To test whether the systemic lack of C3 were responsible for the accelerated elimination of subretinal MP in $Cx3cr1^{GFP/GFP}Cfh^{-/-}$-mice, hepatic Cfh were replaced by hydrodynamic injection of a plasmide encoding Cfh under an albumine promoter four days prior to the light-challenge. ELISA analysis of plasma C3 showed that the Cfh-transfection significantly restored circulating C3 concentrations in $Cx3cr1^{GFP/GFP}Cfh^{-/-}$-mice to 40-60% of the $Cx3cr1^{GFP/GFP}$ levels over the 14 day experimental protocol compared to control plasmid transfected and non-transfected $Cx3cr1^{GFP/GFP}Cfh^{-/-}$-mice (FIG. 3B). However, the significant increase of circulating C3 levels did not increase the number of subretinal MPs (quantified on IBA-1-stained retinal and RPE/choroidal-flatmounts) in $Cx3cr1^{GFP/GFP}Cfh^{-/-}$-mice at d14 (FIG. 3C).

The comparable subretinal MP counts at the beginning of the acute inflammation at d4 (FIG. 3A) and the lack of influence of circulating C3 levels on the MP count in the resolution phase (FIG. 3C) suggested that systemic CFH or C3 was not involved in the recruitment of MPs or responsible for their accelerated elimination in $Cx3cr1^{GFP/GFP}Cfh^{-/-}$-mice. RT-PCRs of relative Cfh expression of retinal and RPE/choroid tissue homogenates, bone marrow- and circulating-monocytes, and brain- and retina-microglial cells (MCs) showed that the RPE/choroid and MCs expressed the highest levels of Cfh mRNA in WT and Cx3cr1$^{GFP/GFP}$-mice (FIG. 3D), in accordance with CFH protein localization around subretinal MPs in vivo (FIG. 4A-D). To evaluate if CFH from MCs or from the RPE influenced subretinal MP elimination we next adoptively transferred CFSE-labeled brain MCs from the different mouse strains into the subretinal space of either wildtype- or Cfh$^{-/-}$ mice and counted the surviving CFSE$^+$ MCs 24h after injection. We previously showed that wildtype MPs, that may be monocytes, MCs or Mφs, are very quickly eliminated from the subretinal space and that the clearance is significantly delayed in Cx3cr1-deficient MPs (Levy et al., EMBO Mol Med. 2015, 7:211-226). Here, results show that Cfh-deficiency significantly increases the rate of elimination of Cx3cr1$^{GFP/GFP}$ MCs and that this difference is reversed by purified human CFH (FIG. 3E). Interestingly, the recipient derived-CFH only had a very minor effect on the MC elimination rate.

Therefore, these results show that MP derived CFH inhibits the elimination of subretinal MCs, which is likely responsible for the observed inhibitory effect of local CFH on the resolution of acute subretinal inflammation observed in vivo.

Example 3: CFH Fixation to CD11b/CD18 Inhibits MP Elimination

Figure 3:
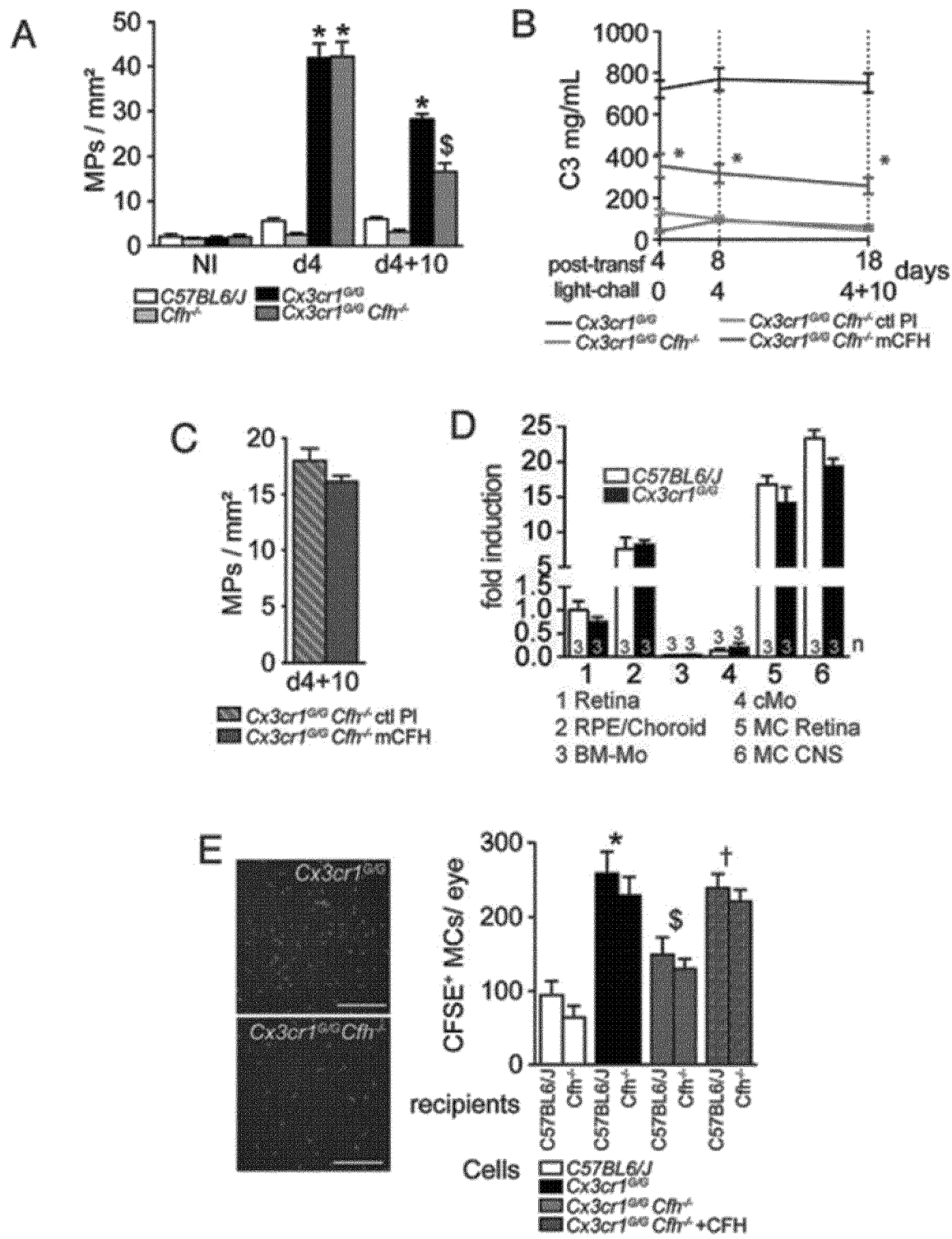
FIG. 3 is a set of graphs showing that MP-derived CFH inhibits the resolution of acute subretinal inflammation. A: Quantification of subretinal IBA-1+ MPs in non-illuminated (NI), 4d-light challenged (d4), and 4d-light challenged followed by 10 recovery days (4+10) of 2-3-month-old mice of the indicated strains. (n=6-12 per group, one way Anova/Bonferroni test *p<0.001 versus the NI groups, $p<0.0001 versus Cx3cr1$^{GFP/GFP}$d4+10;). B: Quantification by ELISA of circulating plasma C3 in 2-3-month-old Cx3cr1$^{GFP/GFP}$, Cx3cr1$^{GFP/GFP}$Cfh$^{-/-}$ mice before (D0), at the end (D4) and ten days after (D14) the light-challenge model. Four days before mice were injected with 100 μg of empty plasmid or expressing murine CFH or not injected. (n=4-5 per group one way Anova/Bonferroni test *p<0.001). C: Quantification of subretinal IBA-1+ MPs/mm² in light-challenge model at day 14 of 2-3-month-old mice Cx3cr1$^{GFP/GFP}$, Cx3cr1$^{GFP/GFP}$Cfh$^{-/-}$ that were injected with 100 μg of empty plasmid or expressing murine CFH (n=6-10 per group one way Anova/Bonferroni test *p<0.001). D: Quantitative RT-PCR of Cfh mRNA normalized with Rps26 mRNA of retina, choroid/RPE, circulating monocytes (cMo), bone marrow monocytes (BM-Mo), retinal microglia (MC Retina), brain microglia from the indicated strains (MC CNS; n=3 preparations from 5 pooled mice). E: Representative micrograph of CFSE+ MCs of the indicated strains, 24h after subretinal adoptive transfer to Cfh$^{-/-}$ mice. Quantification of CFSE+ MCs of the indicated strains, 24h after adoptive transfer to C57BL6/J wildtype or Cfh$^{-/-}$ mice (n=12-18/group; one way Anova/Bonferroni test *p<0.001 versus C57BL6/J wildtype CFSE+ MCs, $p<0.0001 versus Cx3cr1$^{GFP/GFP}$ CFSE+ MCs, †p<0.0001 versus Cx3cr1$^{GFP/GFP}$Cfh$^{-/-}$ CFSE+ MCs). Scale bar=50 μm.
Figure 4:
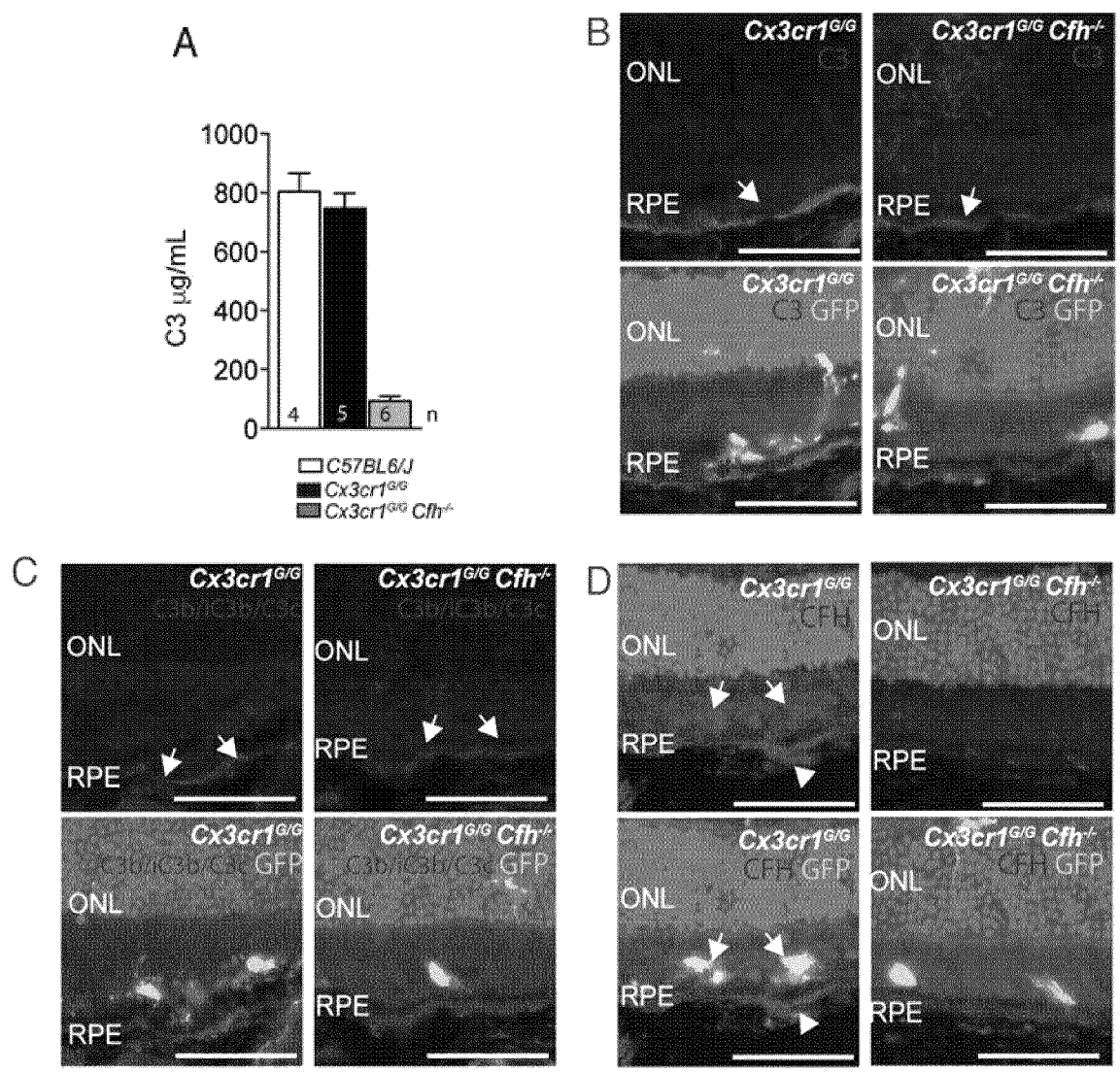
FIG. 4 is a set of graph and photographs showing plasma C3 concentrations and C3, and C3 fragment, and CFH immunohistochemistry in the transgenic mice. A: Complement factor C3 (C3)-ELISA measurements of plasma C3 concentrations from C57BL6/J wildtype, Cx3cr1$^{GFP/GFP}$ or Cx3cr1$^{GFP/GFP}$ Cfh$^{-/-}$ mice. B-D: Immunohistochemistry for C3 (B, clone 11H9 Hycult biotech), C3b/iC3b/C3c (C, clone 3/26 Hycult biotech), and CFH (D, ab8842 Abcam) in 4d light-challenged Cx3cr1$^{GFP/GFP}$ and Cx3cr1$^{GFP/GFP}$ Cfh$^{-/-}$ mice. ONL: outer nuclear layer; RPE retinal pigment epithelium. negative control: omitting the primary antibodies revealed no staining (not shown); the experiment was repeated three times with similar results. Scale bar=50 μm.
Figure 5:
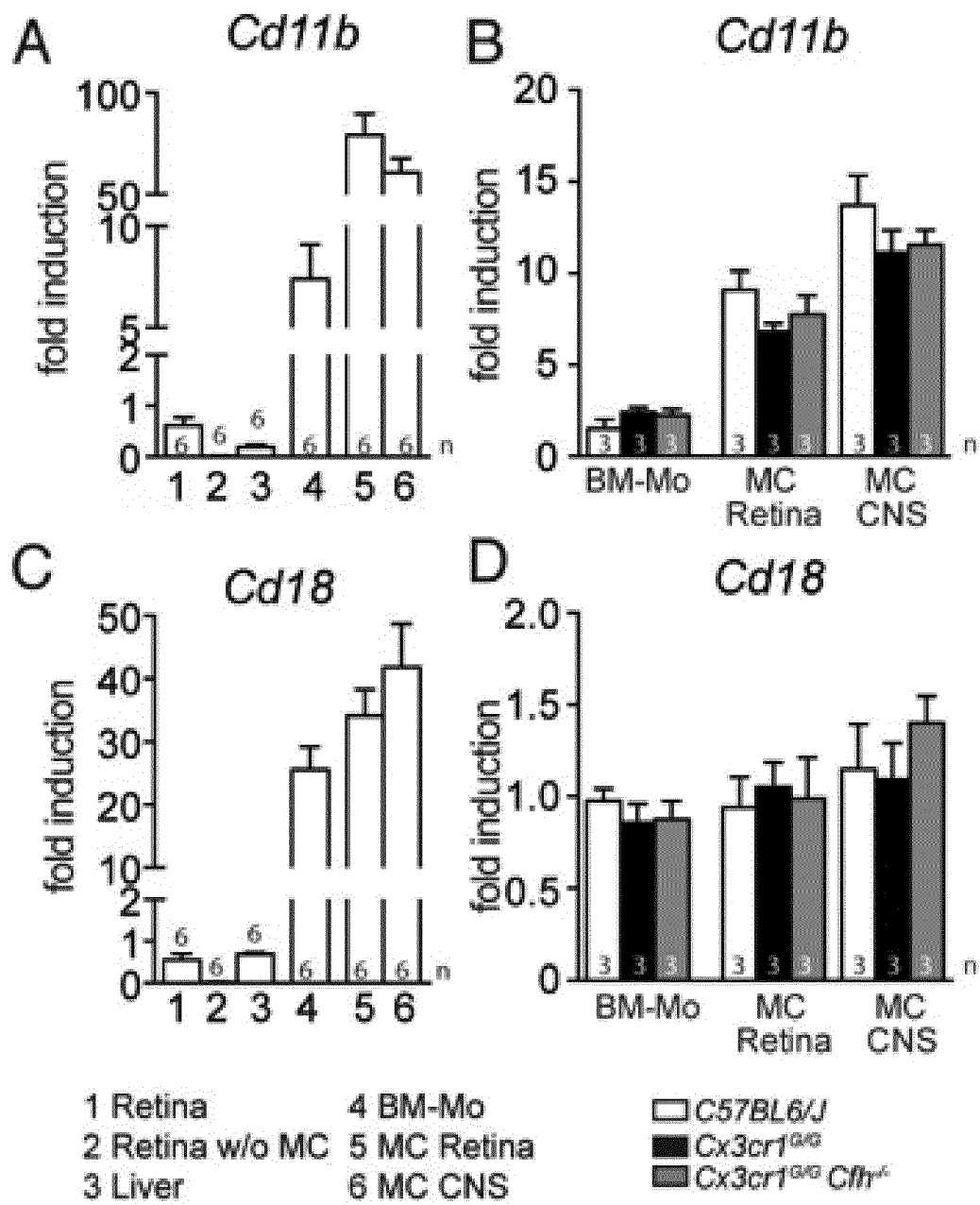
FIG. 5 is a set of graphs showing Cd11b and Cd18 transcription in MPs. Quantitative RT-PCR of Cd11b (A-B), Cd18 (C-D) mRNA, normalized with Rps26 mRNA, in retina (1), retina without MCs (2, after sorting of MCs), liver (3), bone marrow monocytes (BM-Mo), retinal microglia (5, MC Retina) and brain microglia (6, CNS MC) from WT C57BL6/J mice (left column), and of BM-Mo, and MCs from retina and CNS of Cx3cr1$^{GFP/GFP}$ and Cx3cr1$^{GFP/GFP}$ Cfh$^{-/-}$ mice (middle and right column).

The integrins CD11b (ITGAM) and CD18 (ITGB2) form a heterodimer (MAC-1, CR3) that has been shown to bind surface CFH on monocytes and neutrophils. CD11b/CD18 is strongly expressed in MPs with no detectable differences in our different mouse strains (FIG. 5A-N). Flow cytometry of Cx3cr1$^{GFP/GFP}$Cfh$^{-/-}$-MCs, incubated with Cy5 conjugated purified CFH showed that CFH also fixes on the surface of purified MCs (FIG. 6A). Next, negatively sorted Cx3cr1$^{GFP/GFP}$Cfh$^{-/-}$ bone marrow monocytes were pre-incubated with a control IgG2 or the anti-CD11b 5C6 antibody clone prior to Cy3 conjugated CFH incubation. Flow cytometry showed that the anti-CD11b 5C6 clone strongly inhibited the cell surface CFH fixation (FIG. 6B). Interestingly, the anti-CD11b M1/70 clone that is used to purify the MCs did not interfere with CFH binding, demonstrated by the flow cytometry in FIG. 6A and the fact that recombinant CFH is capable to reverse the accelerated elimination of M1/70-sorted Cx3cr1$^{GFP/GFP}$Cfh$^{-/-}$-MCs (FIG. 3). This difference is likely due to the fact that the M1/70 clone recognizes a distinct part of CD11b compared to the 5C6 clone 48. Indeed, blocking the CFH fixation using the anti-CD11b 5C6 IgG in subretinally adoptively transferred Cx3cr1$^{GFP/GFP}$Cfh$^{-/-}$-MCs (wildtype recipients) completely prevented the inhibitory effect of added CFH protein on the elimination rate compared to the control IgG (FIG. 6C). To test whether it is possible to therapeutically speed-up subretinal inflammation resolution, subretinal inflammation in 3-month-old Cx3cr1$^{GFP/GFP}$-mice was induced using a laser burn, which induces significant subretinal MP accumulation peaking at d4 and resolving thereafter (Lavalette et al., Am J Pathol. 2011, 178:2416-2423). Results show that the local, intravitreal injection at d0 of the anti-CD11b 5C6 IgG (to inhibit CFH fixation) significantly reduced the number of subretinal IBA$^+$ MPs around the impact (FIG. 6D) on retinal/RPE flatmounts and the associated neovascularization (FIG. 6E; quantified as CD102 positive area) compared to the control IgG at d7.

These results show that CFH fixes to MC surfaces and that the fixation of CFH to MC CD11b/CD18 is necessary for CFH to inhibit MC elimination. They also demonstrate that the inhibition of the binding of CFH to CD11b/CD18 speeds up MP elimination on the site of inflammation.

Figure 7:
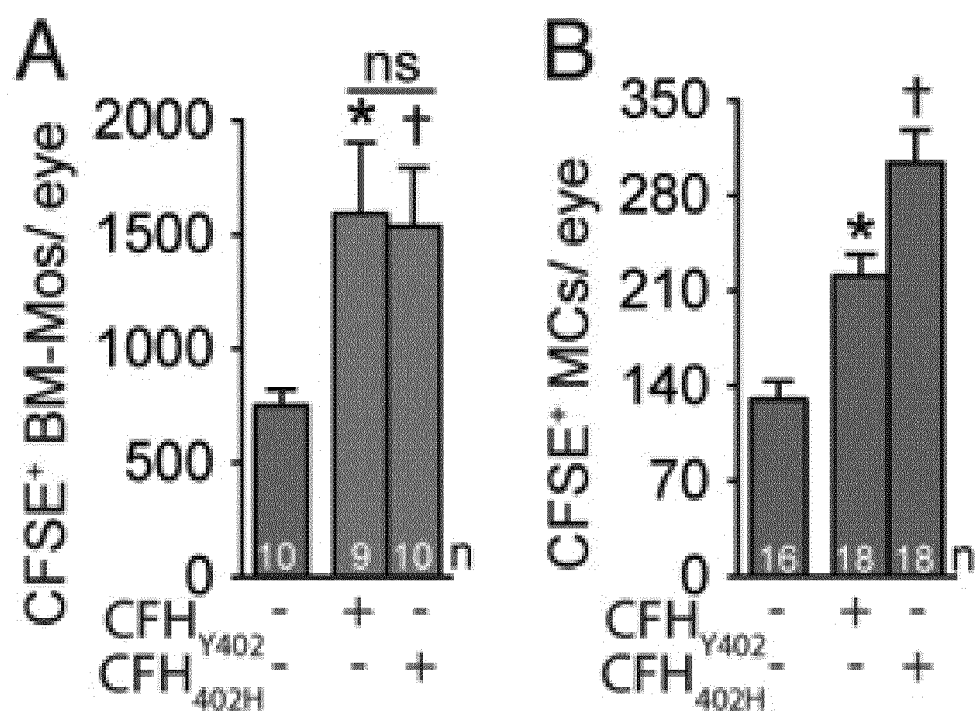
FIG. 7 is a set of histograms showing that the AMD-associated 402H CFH inhibits subretinal MP elimination significantly more than the common 402Y CFH. A: Quantification of subretinal Cx3cr1$^{GFP/GFP}$ Cfh$^{-/-}$ CFSE+ monocytes on RPE and retinal flatmounts 24h after adoptive transfer to WT C57BL6/J mice with and without purified CFH$_{Y402}$ or CFH$_{402H}$ (Anova/Bonferroni test *p<0.0001). B: Quantification of Cx3cr1$^{GFP/GFP}$Cfh$^{-/-}$ CFSE+ MCs on RPE and retina flatmounts with PBS, hCFH 402Y or hCFH 402H (n=18-30 per group, one way Anova/Bonferroni test *p<0.0001). Mos: monocytes; MCs: microglial cells; n=number of replicates indicated in the graphs, replicates represent quantifications from individual mice from two (A) to three (B) experiments with three different cell preparations.

Example 4: The AMD-Associated 402H CFH Inhibits Subretinal MP Elimination Significantly More than the Common 402Y CFH The Y402H polymorphism that is strongly associated with soft drusen and AMD is located in the SCR7 of CFH, which mediates its binding to polyanionic cell surfaces, but also to CD11b/CD18 (Losse et al., J Immunol. 2010, 184: 912-921; Kang et al., Immunobiology. 2012, 217:455-464). To evaluate whether the disease associated 402H CFH differed in its capacity to inhibit subretinal MP elimination from the common 402Y CFH, CFSE-labeled Cx3cr1$^{GFP/GFP}$Cfh$^{-/-}$-MCs were adoptively transferred into the subretinal space of wildtype recipients and co-injected either form of CFH at 500 jtg/ml, which corresponds to the plasma concentration. Subretinal CFSE$^+$ MC counts on RPE/retinal flatmounts 24h after the injection revealed that both isoforms significantly inhibited the MC elimination compared to cells injected without CFH (FIG. 7) and similar to commercially available purified CFH, which likely contains a mixture of both isoforms (see FIG. 6). However, CFSE$^+$ MCs injected with the disease-associated 402H CFH form resisted the clearance significantly more than those injected the common 402Y CFH form (FIG. 7).

Therefore, these results show that the AMD-associated 402H CFH inhibits subretinal MP elimination more strongly than the common 402Y CFH. It might thereby inhibit inflammation resolution and contribute to the chronification of subretinal inflammation in AMD, evidenced by the presence of subretinal MPs observed in patients with soft drusen and late AMD.

The invention claimed is:

1. A method for treating inflammation in a subject comprising administering to the subject an agent inhibiting the binding of Complement Factor H to CD11b/CD18, wherein said agent binds CD11b/CD18 to at least one binding site to Complement Factor H, wherein said agent is an anti-CD11b antibody selected from the group comprising the clone 5C6 and the clone ICRF44 and wherein said inflammation is atrophic age-related macular generation.

2. The method according to claim 1, wherein said inflammation is associated with mononuclear phagocytes accumulation.

3. The method according to claim 1, wherein said agent is topically administered to said subject.

4. A method for treating inflammation in a subject comprising administering to the subject an agent inhibiting the binding of Complement Factor H to CD11b/CD18, wherein said agent binds CD11b/CD18 to at least one binding site to Complement Factor H, wherein said agent is an anti-CD18 antibody selected from the group comprising erlizumab and the clone L130 and wherein said inflammation is atrophic age-related macular generation.

5. The method according to claim 4, wherein said inflammation is associated with mononuclear phagocytes accumulation.

6. The method according to claim 4, wherein said agent is topically administered to said subject.

* * * * *